(12) United States Patent
Schoenig et al.

(10) Patent No.: US 10,299,875 B2
(45) Date of Patent: May 28, 2019

(54) DEVICES FOR MOBILITY ASSISTANCE AND INFUSION MANAGEMENT

(71) Applicant: Firefly Medical, Inc., Fort Collins, CO (US)

(72) Inventors: Darrell Schoenig, Bellvue, CO (US); Stephen E. Schmutzer, Fort Collins, CO (US)

(73) Assignee: Firefly Medical, Inc., Fort Collins, CO (US)

( * ) Notice: Subject to any disclaimer, the term of this patent is extended or adjusted under 35 U.S.C. 154(b) by 81 days.

(21) Appl. No.: 14/905,113

(22) PCT Filed: Jul. 18, 2014

(86) PCT No.: PCT/US2014/047254
§ 371 (c)(1),
(2) Date: Jan. 14, 2016

(87) PCT Pub. No.: WO2015/010060
PCT Pub. Date: Jan. 22, 2015

(65) Prior Publication Data
US 2016/0157951 A1 Jun. 9, 2016

Related U.S. Application Data

(60) Provisional application No. 61/856,431, filed on Jul. 19, 2013, provisional application No. 61/880,644, (Continued)

(51) Int. Cl.
*A61G 12/00* (2006.01)
*A61M 5/14* (2006.01)
(Continued)

(52) U.S. Cl.
CPC ............. *A61B 50/13* (2016.02); *A61G 7/0503* (2013.01); *A61H 3/04* (2013.01); *A61M 5/1415* (2013.01);
(Continued)

(58) Field of Classification Search
CPC .................... A61H 3/04; A61H 7/0503; A61H 2003/0022; A61H 2003/002; A61B 50/13;
(Continued)

(56) References Cited

U.S. PATENT DOCUMENTS

| 907,171 A | 12/1908 | Poles et al. |
| D45,770 S | 5/1914 | Shaw |

(Continued)

FOREIGN PATENT DOCUMENTS

| JP | S49-062892 | 6/1974 |
| JP | H01-284250 | 11/1989 |

(Continued)

OTHER PUBLICATIONS

Extended European Search Report, EP 14826018.5, dated Feb. 7, 2017, 8 pages.
(Continued)

*Primary Examiner* — Anne Marie M Boehler
(74) *Attorney, Agent, or Firm* — Leydig, Voit & Mayer, Ltd.

(57) ABSTRACT

Provided are mobility assistance devices, particularly useful in medical settings where a patient ambulation is desired but the patient remains connected to one or many medical components. The system comprises a mast connected to a base, wherein the mast is angled with respect to the base and from which any number of medical components is supported. The device geometry and connections ensure the device is extremely stable and tip-resistant. Also provided are oxygen tank holders to reliably and conveniently hold
(Continued)

oxygen tanks and power management systems that reliably provide electrical power without impacting device performance or mobility. The device is deployable to permit conversion between a compact storage configuration and a stable deployed configuration.

22 Claims, 35 Drawing Sheets

Related U.S. Application Data filed on Sep. 20, 2013, provisional application No. 61/947,809, filed on Mar. 4, 2014.

(51) Int. Cl.

| | |
|---|---|
| *B62B 3/02* | (2006.01) |
| *A61B 50/13* | (2016.01) |
| *A61G 7/05* | (2006.01) |
| *A61H 3/04* | (2006.01) |
| *B62B 5/00* | (2006.01) |
| *F16M 11/28* | (2006.01) |
| *F16M 11/38* | (2006.01) |
| *F16M 11/42* | (2006.01) |
| *A61G 7/10* | (2006.01) |
| *A61H 3/00* | (2006.01) |

(52) U.S. Cl.
CPC ............ *A61M 5/1418* (2013.01); *B62B 3/02* (2013.01); *B62B 5/002* (2013.01); *F16M 11/28* (2013.01); *F16M 11/38* (2013.01); *F16M 11/42* (2013.01); *A61G 7/1046* (2013.01); *A61H 2003/002* (2013.01); *A61H 2201/0192* (2013.01)

(58) Field of Classification Search
CPC .. A61B 5/1415; A61B 5/1418; A61M 5/1415; A61M 5/1418; F16M 11/38; F16M 11/42; F16M 11/28; A61G 12/008; A61G 12/002; A61G 7/0503; A61G 7/1046; B62B 3/02; B62B 3/12; B62B 5/002; B62B 5/02
See application file for complete search history.

(56) References Cited

U.S. PATENT DOCUMENTS

| | | | |
|---|---|---|---|
| 1,612,148 A | 12/1926 | Oettinger | |
| 2,583,114 A | 1/1952 | Monteith | |
| 2,596,055 A | 5/1952 | Thomas | |
| 2,794,612 A | 6/1957 | Clifton | |
| 2,795,387 A | 6/1957 | Elsey | |
| 3,437,296 A | 4/1969 | Hinz | |
| 3,533,583 A | 10/1970 | Azim | |
| 3,719,789 A | 3/1973 | Harnden, Jr. | |
| 4,251,044 A | 2/1981 | Olson | |
| 4,266,765 A * | 5/1981 | Sandoval | A61G 12/00 280/47.371 |
| 4,332,378 A | 6/1982 | Pryor | |
| 4,341,381 A | 7/1982 | Norberg | |
| 4,541,596 A | 9/1985 | Price | |
| D281,453 S | 11/1985 | DiGianfilippo et al. | |
| 4,725,027 A | 2/1988 | Bekanich | |
| 4,744,536 A | 5/1988 | Bancalari | |
| D298,460 S | 11/1988 | Pryor | |
| 4,807,837 A | 2/1989 | Gawlik et al. | |
| 4,832,294 A | 5/1989 | Eidem | |
| 4,867,273 A | 9/1989 | Schaevitz | |
| 4,892,279 A | 1/1990 | Lafferty et al. | |
| 4,905,944 A | 3/1990 | Jost et al. | |
| 4,907,794 A | 3/1990 | Rose | |
| D310,570 S | 9/1990 | Wells | |
| 5,167,389 A | 12/1992 | Reimers | |
| 5,411,044 A | 5/1995 | Andolfi | |
| 5,458,305 A | 10/1995 | Woodward | |
| 5,479,953 A | 1/1996 | Pasulka | |
| 5,526,894 A | 6/1996 | Wang | |
| 5,556,065 A | 9/1996 | Wadley | |
| 5,617,958 A | 4/1997 | Laug et al. | |
| 5,622,344 A | 4/1997 | Gracie | |
| D385,348 S | 10/1997 | Ward et al. | |
| 5,704,577 A | 1/1998 | Gordon | |
| D390,953 S | 2/1998 | Ward et al. | |
| 5,772,162 A | 6/1998 | Lin | |
| 6,056,249 A | 5/2000 | Fillon | |
| D434,495 S | 11/2000 | Whalen | |
| 6,161,850 A | 12/2000 | James et al. | |
| D436,167 S | 1/2001 | Ebert | |
| 6,209,829 B1 | 4/2001 | Yu | |
| 6,226,833 B1 | 5/2001 | Kawaguchi et al. | |
| 6,296,260 B1 | 10/2001 | Schiavone | |
| 6,296,263 B1 | 10/2001 | Schultz et al. | |
| D457,239 S | 5/2002 | Kunik | |
| 6,430,761 B1 | 8/2002 | Brandorff et al. | |
| 6,467,797 B1 | 10/2002 | Lofy et al. | |
| D479,164 S | 9/2003 | Wu | |
| 6,619,599 B2 | 9/2003 | Elliot et al. | |
| 6,698,789 B2 | 3/2004 | Reimers et al. | |
| 6,839,939 B2 | 1/2005 | Donakowski | |
| D503,909 S | 4/2005 | Tolfsen et al. | |
| 6,899,660 B1 | 5/2005 | Chin et al. | |
| 6,969,031 B2 | 11/2005 | Ugent et al. | |
| 6,983,915 B2 | 1/2006 | Adelman | |
| D519,423 S | 4/2006 | Tolfsen | |
| 7,048,222 B1 | 5/2006 | Curtiss | |
| 7,065,812 B2 | 6/2006 | Newkirk et al. | |
| 7,118,079 B2 | 10/2006 | Kung | |
| 7,278,615 B2 | 10/2007 | Schubert et al. | |
| 7,281,691 B2 | 10/2007 | Adelman | |
| 7,353,731 B2 | 4/2008 | Lin | |
| D568,467 S | 5/2008 | Cottone | |
| 7,591,479 B2 | 9/2009 | Golias | |
| 7,634,824 B2 | 12/2009 | Gramkow et al. | |
| 7,726,327 B2 | 6/2010 | Battiston | |
| D622,377 S | 8/2010 | Jackson | |
| D627,063 S | 11/2010 | West et al. | |
| D628,691 S | 12/2010 | Sung et al. | |
| D630,731 S | 1/2011 | Schmutzer et al. | |
| 7,918,422 B2 * | 4/2011 | Blankenship | A61M 5/1415 248/129 |
| 7,935,030 B1 | 5/2011 | Nesbitt | |
| 8,136,773 B2 | 3/2012 | Schmutzer et al. | |
| 8,292,310 B2 * | 10/2012 | Turner | A61H 3/04 280/47.34 |
| 8,403,275 B2 * | 3/2013 | Cote | A61M 5/1415 211/85.18 |
| 8,534,616 B2 | 9/2013 | Schmutzer et al. | |
| 8,662,458 B2 | 3/2014 | Henault | |
| 9,173,803 B2 | 11/2015 | Schmutzer et al. | |
| 2003/0178538 A1 | 9/2003 | Hasloecher et al. | |
| 2005/0139736 A1 | 6/2005 | Breda et al. | |
| 2005/0230573 A1 | 10/2005 | Ligertwood | |
| 2006/0001226 A1 | 1/2006 | Refsum | |
| 2007/0267551 A1 | 11/2007 | Townsend | |
| 2008/0156946 A1 | 7/2008 | Schmutzer et al. | |
| 2008/0176720 A1 * | 7/2008 | Vanmanshoven | A61H 3/04 482/68 |
| 2008/0210831 A1 | 9/2008 | Considine | |
| 2009/0314923 A1 * | 12/2009 | Timoszyk | A61M 5/1415 248/647 |
| 2010/0303603 A1 * | 12/2010 | Galante | A47B 97/00 414/811 |
| 2011/0016628 A1 | 1/2011 | Masterson | |
| 2011/0023920 A1 | 2/2011 | Bolton | |
| 2011/0030749 A1 | 2/2011 | Miller | |
| 2011/0290979 A1 | 12/2011 | Henault et al. | |
| 2012/0133111 A1 | 5/2012 | Schmutzer et al. | |
| 2013/0181100 A1 * | 7/2013 | Blankenship | A61M 5/1415 248/129 |

(56) References Cited

U.S. PATENT DOCUMENTS

| | | | |
|---|---|---|---|
| 2013/0270799 A1 | 10/2013 | Schmutzer et al. | |
| 2014/0068855 A1* | 3/2014 | Grow .................. | A61G 7/1017 5/87.1 |
| 2016/0114102 A1* | 4/2016 | Yamamoto .......... | A61M 5/1415 108/27 |

FOREIGN PATENT DOCUMENTS

| | | |
|---|---|---|
| JP | H03-046338 | 4/1991 |
| JP | 3040162 | 8/1997 |
| JP | 2002-211405 | 7/2002 |
| JP | 2005-506244 | 3/2005 |
| JP | 2006-335355 | 12/2006 |
| WO | WO 2004/101034 | 11/2004 |
| WO | WO 2008/085698 | 7/2008 |

OTHER PUBLICATIONS

First Office Action, CN 2014800519191, with English Translation, dated Dec. 27, 2016, 20 pages.

Blickman Catalog, Nezzie Ambulation Device, http://www.blickman.com/products/0429000000—3 pages, accessed Mar. 2, 2015.

LivenGood PACE, http://www.livengoodmed.com/—5 pages, accessed Mar. 10, 2015.

European Search Report and Opinion corresponding to European Patent Application No. 2007869691, dated Feb. 9, 2015.

International Search Report with Written Opinion corresponding to International Patent Application No. PCT/US2007/088433, dated Aug. 7, 2008.

International Search Report with Written Opinion corresponding to International Patent Application No. PCT/US2014/047254, dated Nov. 12, 2014.

Office Action corresponding to Australian Patent Application No. 2007342126, dated Jul. 25, 2012.

Office Action corresponding to Japanese Patent Application No. P2009-544881, dispatched Aug. 6, 2013—with English translation.

Office Action corresponding to Japanese Patent Application No. P2009-544881, dispatched Jul. 3, 2012—with English translation.

Office Action corresponding to Japanese Patent Application No. P2013-252977, dispatched Oct. 14, 2014—with English translation.

* cited by examiner

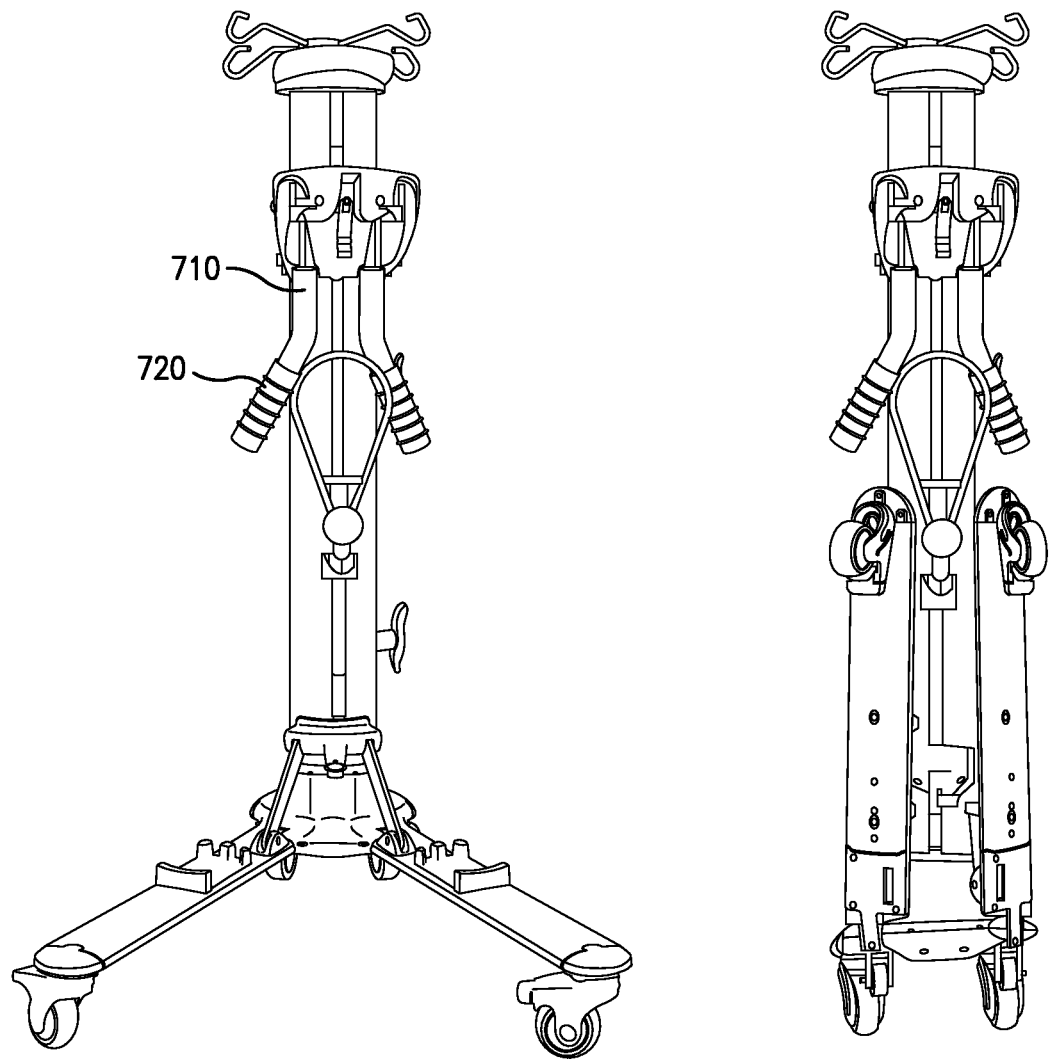
FIG. 25  FIG. 26

DEVICES FOR MOBILITY ASSISTANCE AND INFUSION MANAGEMENT

CROSS-REFERENCE TO RELATED APPLICATIONS

This application claims the benefit of and priority to U.S. Provisional Patent App. Nos. 61/947,809 filed Mar. 4, 2014 (91-13P1), 61/880,644 filed Sep. 20, 2013 (91-13P) and 61/856,431 filed Jul. 19, 2013 (173-06P1), each of which is hereby incorporate by reference to the extent not inconsistent herewith.

BACKGROUND OF THE INVENTION

The invention is generally in the field of a mobile support stand that is capable of folding into a compact storage configuration, and has specific applications in the medical field, including providing mobility assistance to a person connected to an infusion pump and attendant medical components. Accordingly, the device is useful as a mobility assistance device to a person in a medical setting. As discussed in U.S. Pat. Nos. 8,136,773 and 8,534,616, it is important for patient rehabilitation and recovery that a patient be able to walk, even when connected to a medical component, after a medical procedure. A walking patient, however, presents special safety problems in terms of ensuring the supporting pole is stable and does not tip or hinder the patient or caregiver when it is moving with the patient. This safety concern is not adequately addressed by current IV poles that have a vertical pole connected to a wheeled base. There remains a need in the art to secure relatively heavy components, as well as other lighter but necessary components (e.g., IV fluids), easily and reliably to a device in a manner that allows ready access to the components attached to the IV pole. Because many patients also require external oxygen support, there is also a need to reliably secure oxygen sources in a reliable manner without adversely impacting patient or device maneuverability. Furthermore, electrical power is often desired to power any one or more components connected to the mobility assistance device. Disclosed herein are devices that achieve these objectives while further improving device stability and maneuverability for a user connected to the medical components and ambulating the device. Furthermore, the devices provided herein are capable of folding into an extremely compact configuration when not in use.

SUMMARY OF THE INVENTION

Provided herein is a mobility assistance device (also referred herein as an infusion management system or IMS) particularly suited to facilitating safe and reliable ambulation by persons connected to devices, such as a patient receiving medical treatment including IV infusion. The devices provided herein specifically address needs of medical caregivers and enhance patient care while promoting safe patient ambulation. The advantages of the devices provided herein include improved safety for both patients and staff by the device's superior stability, security and comfort. All these advantages result in minimized risk and costs associated with patient falls. The devices provide easier, quicker and more reliable ambulation to facilitate recovery and minimize risk of falls. Furthermore, medical caregiver workload is reduced and time is saved as the device permits one caregiver to do the work of the current two or three caregivers who use conventional systems. The instant device is easy to fold into a stored configuration when not in use. The device can store underneath furniture, such as a bed, or be secured against a vertical surface. This keeps rooms tidy and traffic areas clear and further assists with facility compliance.

In an aspect, the mobility assistance device comprises a mast having a top end, a bottom end and an outer surface extending between the top and bottom ends. A base comprising a first base leg and a second base leg to form a two-sided base footprint is connected to the mast, such as at one end of each of the first and second base legs that connect to the mast. This connection region is referred herein as a "vertex region". In an aspect, the vertex region is toward the bottom or at the bottom of the mast in embodiments where the base legs connect near the bottom of the mast. In an aspect, the vertex region may extend above the bottom portion of the mast such as for base legs that connect at a longitudinal distance from the mast bottom. The vertex region may have a smooth and gently curving outer circumference, thereby minimizing or avoiding sharp angles that can catch or cause damage. The mast and base footprint form a mast angle, wherein the mast angle is an acute angle so that at least a portion of the mast extends within a region that vertically extends from the two-sided base footprint. In contrast, if the mast is straight-line linear and at a right angle relative to the base, the mast is not considered to extend within a region that vertically extends from the two-sided base footprint. A pole connects to the mast for securing a medical component, wherein the pole has a longitudinal axis or an outer surface that is separated from the mast outer surface by a separation distance. The pole is particularly suited for securing or clamping an infusion pump in a manner that provides ease of use, readability and attachment without sacrificing device stability and maneuverability. A mobility handle is connected to the mast, base, or the vertex region. The particular point of attachment is not critical, so long as device stability is maintained during ambulation. In an aspect the mobility handle(s) connect to the mast.

To facilitate device maneuverability, a first wheel is connected to the first base leg, a second wheel is connected to the second base leg and a third wheel is connected to the vertex region. Optionally, a fourth wheel is connected to the vertex region. Each of the wheels are configured and positioned to stably contact a supporting surface on which the device rests and the mobility handle is configured to receive an applied force to stably ambulate the device over the supporting surface. Accordingly, in an aspect the wheels are positioned at a base leg end that is separated from the vertex region by at least 80%, at least 90%, or substantially all the longitudinal length of the base leg.

In an aspect, the pole is extendible to provide a pole top end that is controllably extended from the mast top end. This is useful for those embodiments where the pole further supports one or more medical components at a top end of the pole and it is desired to position those medical components at different heights depending on operating conditions.

In an aspect, the pole is substantially aligned with a longitudinal axis of the mast, the mast outer surface, or both. For example, when the mast outer surface is parallel to the mast longitudinal axis, the pole may be parallel thereto. In contrast, when the mast outer surface is curved, the pole may match the mast longitudinal axis instead of the curves of the mast outer surface. "Longitudinal axis" refers to the axis of the central portion of a longitudinally-extending member. Alternatively, the pole may also be curved to match the curve of the mast outer surface. In another aspect, the pole may have a curve that does not match the mast surface, such as to provide a handle for a caregiver to help control device movement or to place a medical component in a desired location.

Alternatively, the pole is substantially vertical with respect to the two-sided base footprint and positioned within the region that vertically extends from the two-sided base footprint. In this embodiment, the pole may connect to a portion of the mast that itself is positioned within a region that extends vertically from the base legs so as to maintain good stability.

In an aspect, the pole is connected to a top portion of the mast and/or a bottom portion of the mast. For example, the connection between the pole and top portion of the mast may comprise a top connector that extends from the mast top end and has a passage for receiving the pole.

In an embodiment, the pole comprises an upper pole portion and a lower pole portion, wherein the upper and lower pole portions are telescopingly connected to provide a pole length that is adjustable by movement of the upper pole portion relative to the mast, including the top connector and the bottom portion of the pole. In an aspect, a bottom connector secures the bottom portion of the extendible pole to the mast bottom end.

Any of the devices provided herein may further comprise a quick release clamp operably connecting the upper and lower pole portions for controlling the pole length. The release clamp is released to permit movement of the upper pole portion and, at a desired position, the clamp is engaged to reliably position the pole top end.

In an aspect, the extendible pole has a top end that is controllably positioned with respect to the mast top end and is further defined in terms of a selectable separation distance from the mast top end that is greater than or equal to 0 cm (corresponding to a pole-stored configuration) and less than or equal to 1 m.

In an embodiment, any of the devices provided herein further comprise a holder or a plurality of holders connected to the pole top end for securing a medical component. The plurality of holders may each extend from the pole top end in a non-forward facing direction. One example of a non-forward facing placement is a first and second holder that are extendably opposed to each other in a left and a right direction relative to the device, and at least two additional holders are evenly rotationally spaced and extend in a rearward-facing direction. In this manner, each holder is evenly separated from adjacent holders, but only span the rearward facing 180°, so that four holders are rotationally separated by 60°, In an aspect where there are three holders, the holders are rotationally separated by 90°. Each holder may terminate in a hook geometry. In an aspect, the holders are rotationally and/or removably connected to the pole top end. In the aspect where the holders are rotationally connected, the holders may be rotated as desired relative to the mast so as to minimize interference with a patient and/or caregiver. The rotation may provide a continuously positional holder configuration over an entire 360° circumferential position. For example, the holders may be positioned forward to minimize patient obstruction during use. In contrast, during storage, the holders may be positioned in the rearward facing direction to provide maximum compactness, such as for shipping or to avoid overly exposed hooks facing in an outward direction. The holders may also be positioned in a left or right side facing direction, such as to minimize interference with a person walking alongside the device and patient.

In an aspect, any of the devices provided are further characterized in terms of the mast angle, such as a mast angle selected from a range that is greater than or equal to 50° and less than or equal to 85°, or about 70°.

In an aspect, the extendible pole has at least one holder at a top end of the extendible pole and at least one holder at a bottom end of the extendible pole. In this manner, any of the devices provided herein may support at least one medical component at a top portion and at least one medical component at a bottom portion.

In an aspect where the pole is not substantially parallel to the mast or mast surface, the bottom end of the pole may extend to a position that is vertically beneath the mobility handle and optionally coincident to at least a portion of the mobility handle. Similarly, the top end of the pole may extend to a position that is vertically above the mast top end and situated coincident to or in front of the mobility handle.

Any of the devices provided herein may employ additional wheels to provide added versatility depending on device status, such as a deployed configuration or stored/collapsed configuration. For example, any of the devices provided herein may further comprise a fourth wheel connected to the vertex region, wherein the third and fourth wheels are aligned with respect to each other and separated by a separation distance that is greater than or equal to 5 cm and less than or equal to 50 cm. One function of the third and fourth wheels is to improve device maneuverability and control during ambulation. One function of the third and fourth wheels is to improve device stability, including increased tip resistance.

Any of the devices provided herein further comprise a fifth wheel connected to the vertex region or the base, wherein the fifth wheel is in a rearward-offset position relative to the third wheel (and fourth, when present) and vertically offset from each of the first, second and third wheels (and fourth, when present) so that during ambulation the first through third (and fourth, if present) wheels stably contact the support surface and the fifth wheel does not contact the support surface. In this aspect, when the device is in a stored configuration with the base legs positioned substantially adjacent to the mast, the first, second, and fifth wheels stable contact a supporting surface and the third (and fourth, if present) wheel is vertically offset from and not in contact with the support surface, thereby providing controlled movement of the device when the device is in a stored configuration and under an applied force. Wheels (e.g., one or a pair of wheels such as fifth or fifth and sixth wheels are connected to the bottom of the mast, such as at the vertex region, and may be referred herein as "trolley wheels." The trolley wheels are designed to assist mobility of the folded device such as by application of a lifting force at the top end of the mast so as to move the folded device in a manner similar to that of a way two-wheeled trolley suitcase. In contrast, when the device is deployed, the trolley wheels do not contact the support surface. In this manner, the first and second wheels and the trolley wheels may contact the floor in a device-stored configuration. A person may start trolleying the device by lifting the top of the mast very slightly, such as about 0.1°. Then, at about 35°-45° (e.g., 40°) from the floor, wheels three and four (nose casters) contact the floor. However, due to their skewed angle, they freely rotate (swivel) until the mast reaches about 50°-55° (e.g., 53°), at which point they begin bearing the weight of the device. Past that point, the trolley wheels begin to lift off the floor.

In another aspect, any of the devices provided herein further comprise a fifth wheel and a sixth wheel connected to the first and the second base leg, respectively, wherein during ambulation with the device legs deployed, each of the first, second, third and fourth wheels stably contact the support surface and the fifth wheel and the sixth wheel are vertically offset and so do not contact the support surface. In this aspect, the device in a stored configuration is configured so that the fifth wheel and sixth wheels each contact the support surface, and optionally along with the first and second wheels facilitate device maneuverability over the support surface in the stored configuration. This is particularly useful for facilitating device storage in confined spaces, such as under a bed or shelf, where the device may be reliably controlled and steered such as without bending over by a foot or touch without having to lift the device. When the desired storage position is reached, the first and/or second wheels may be locked in position (braked) to prevent inadvertent movement of the device. In this aspect, the large and stable deployed device is provided as a confined and stable device that may be readily maneuvered without excessive force or strength by the user or a caregiver. The front two wheel pairs (e.g., third/fourth and fifth/sixth wheels) are offset with respect to each other. This facilitates stable movement in the deployed configuration as well as the stored configuration, with four wheels contacting the support surface in either configuration. In the deployed configuration, the first/second and third/fourth wheel pairs contact the supporting surface (and the fifth/sixth wheels do not); whereas in the storage configuration, the first/second and fifth/sixth wheel pairs contact the surface (and the third/fourth wheels do not). The particular point of attachment of the fifth and sixth wheels is not important, so long as the attachment point does not prevent the wheels from being offset with respect to the third (and fourth) wheels when the device is deployed and aligned with the first and second wheels when the base legs are in a stored configuration. Accordingly, the fifth and six wheels may be connected to the mast, the vertex region, the base legs, and any portions therein. In an aspect, the fifth and sixth wheels connect to an inner portion of the base legs and are capable of directional swiveling. Alternatively, as described above, the fifth and sixth wheels may be arranged so that they only stably contact the support surface in a device stored configuration and with a lifting motion of the top of the mast so that the mast is sufficiently tilted. In an aspect, a tilt angle of the mast for a device in a stored configuration that is greater than 0° and less than 60° relative to the support surface ensures the fifth and sixth wheels (trolley wheels) engage with the support surface.

Any of the devices may further comprise a mounting arm connected to the mast and extending in a direction that is within the region that vertically extends from the two-sided base footprint, such as for supporting a medical component, including components associated with patients who are recovering from surgery such as a pleur-evac drainage unit that is connected to a patient's chest tube. Similar to the base legs and mobility handle, the mounting arm may be rotably connected to the mast to provide a mounting arm deployed configuration and a mounting arm stored configuration.

Any of the devices herein may be further described in terms of the mobility handle. The mobility handle is an important feature of the mobility assistance device as it is the contact point(s) with the user who is, in turn, connected to various medical component(s) supported by the device. Accordingly, it is important the user be comfortable with the mobility handle configuration and position. With this in mind, any of the devices have a mobility handle that is height adjustable. For example, the height adjustability can be by a translational connection with the mast, such as a mobility handle that longitudinally translates over at least a longitudinal portion of the mast between the top end and the bottom end to provide height adjustability of the mobility handle. Alternatively, via a rotation motion a portion of the mobility handle may be height adjustable similar to a crank that rotates about an axis.

In an embodiment, the translational connection between the mobility handle and the mast comprises a groove in the outer surface of the mast and a mobility handle member that operably engages the groove to releasably position the mobility at a desired height from the base. The mobility handle translationally connected to the mast optionally provides a controllable height adjustability selected from a vertical height relative to the base legs that is greater than or equal to 2 feet and less than or equal to 6 feet. In this manner, the device may be tailored to the user height, ranging from a child to tall adults, thereby ensuring maximum comfort and controllability. Height adjustability may be engaged via a quick-release clamp operably connecting the mobility handle to the trunk.

The mobility handles of the instant device provide the capacity for further useful functionality. For example, the mobility handle may further comprise a platform having a first platform end and a second platform end oppositely configured to each other. A first grip handle connects to the second platform end and a second grip handle connects to the second platform end. The grip handles contain a grip configured to receive a hand of a user who will move and ambulate with the device. The first platform end is translationally connected to the mast to provide longitudinal translation along the mast, thereby providing vertical adjustability to the first and second grip handles. In this manner, the first and second grip handles are configured to receive an ambulation force from a user first hand and a user second hand and the platform may be used to support additional items, such as medical components, mobile computing or communication devices, liquid containers with optionally a container holder such as a cup-holder, and/or the user's personal effects. The platform is extremely versatile and can have any number of geometric shapes, sizes, and configurations. Optionally, a lip may be provided around an outer edge of the platform to prevent materials placed on the platform from falling off the platform.

To enhance device collapsibility, storability and/or shipability, any of the device elements provided herein may be removably or deployably connected to other elements of the device. For example, the first and second grip handles may be removably or rotably connected to the platform, thereby providing a grip handle deployed configuration and a grip handle stored configuration. Alternatively, the platform itself may be rotably connected to the mast.

In an aspect, the first and second grip handles extend from the platform along a plane that is substantially parallel to a base plane defined by the first and second base legs. This is advantageous as it provides the ability to incorporate a reasonably-sized platform in the device without impacting device functionality, mobility, storability or collapsibility. Accordingly, the entire mobility handle vertically translates relative to the base, thereby maintaining good platform alignment with the base and support surface.

In an embodiment, the first and second grip handles are positioned within an area that vertically coincides to the two-sided base footprint. "An area that vertically coincides to the two-sided base footprint" refers to the volume of space that extends above the base footprint with an outer limit defined by the base legs. Depending on the user, however, the invention is not so limited in that the highly stable configuration permits tolerance to the placement of the grip handles outside the region of space defined by the two-sided base footprint. Limitations on the grip handle placement and geometry include ensuring a force applied by a user on a grip handle is insufficient to break, tip or otherwise unbalance the device. This is based on the requirement that one grip handle be capable of supporting a substantial fraction of a user weight in the event the user trips or stumbles and uses one grip handle to prevent a fall. In an aspect, the device is constructed to support a weight of about 200 pounds with at least a safety factor of 1.5, so that an up to 300 lbf can be applied to the device without device breakage or device tipping. In an aspect, the device is configured to accommodate much higher patient weights and corresponding forces.

The mobility handle optionally comprises a first grip handle and a second grip handle that are each linear and extend from the mast at a grip angle that is an acute angle, such as a grip angle selected from a range that is greater than or equal to 30° and less than 90°.

In an aspect, the first grip handle is substantially aligned with the first base leg and the second grip handle is substantially aligned with the second base leg.

To maximize platform stability and usability and minimize potential pinch points, the first platform end is optionally shaped to conform to a shape of a portion of the mast outer surface engaged by the first platform end. Conform in this aspect refers to no more than 2 cm, 1 cm, or 0.5 cm separation from the outer surface of the mast.

Preferably, the mast comprises an inward-facing surface that faces the two-sided base footprint and the first platform end engages the inward-facing surface. Accordingly, the mast may further comprise a front-facing surface that faces toward the front of the device. Optionally, the longitudinally-directed pole surface is separated from the front-facing surface of the mast by a separation distance over substantially the entire pole bottom portion or a middle portion thereof.

Any of the devices provided herein have a first and second base leg that are rotably connected to the mast bottom end to provide a stored configuration wherein the base legs are substantially parallel to the mast and a deployed configuration wherein the base legs and mast form the mast angle acute angle. In an aspect, the base legs have a length that is less than or equal to the mast length. In an aspect, the length of the base legs is between about 40% and 80%, greater than 50%, or between about 50% and 90% the length of the mast.

The rotable connection is by any means known in the art. In an aspect, an engagement pin may be used to engage with various passages to provide a base deployed and base stored configuration. Preferably, however, the deployment may be semi-automated such as the first and second base legs that rotably connect to the mast bottom end by a gas spring that generates a deployment force to deploy the base legs. In this aspect, a storage force is required to store the base legs, and the storage force is greater than the deployment force. This may help prevent inadvertent collapse.

To further increase safety against unintentional collapse, any of the devices may further comprise an anti-collapse mechanism to prevent inadvertent collapse/storage of the base into the stored configuration. Examples of anti-collapse mechanisms include a safety lever that must be released before the base can be stored from a deployed configuration, pins, locks, and the like, including duplicate mechanisms that require simultaneous engagement of two different elements spaced sufficiently far apart to require two physically-distinct storage forces, thereby providing a two-force anti-collapse mechanism.

One important functional benefit of the devices provided herein is the ability to secure an infusion pump to the extendible pole at an off-horizontal or off-vertical angle. This allows the pump display to face outward and at an angle making the pump control more accessible. All other IV poles on the market based on the upright pole configuration, require vertical mounting of the infusion pumps, with attendant disadvantages for pump control access.

The ability to easily and efficiently collapse the device into a confined volume is particularly advantageous for storage. Furthermore, any of the devices herein may be shipped using standard shipment containers. Any of the devices provided herein may be described as having a stored configuration and a deployed configuration, wherein the stored configuration has a storage volume dimension that is less than or equal to 52.25" (length)×12" (height)×10.5" (width) without mechanical removal/separation of any portions of the device. In an aspect, the storage volume is about 50" by 10.5" by 10" to provide a stored volume of about 5250 inches$^3$. In contrast, the corresponding deployed volume dimension corresponds to a length of about 30" by a height of 48" (unextended pole) or 80" (with an extended pole) by 27" to provide a deployed volume of 38,880 inches$^3$ or 64,800 inches$^3$. There are certain variation tolerances in these dimensions, such as from the specific start and end points at which each dimension is measured. A particular advantage of the devices provided herein is the ability to compactly ship a fully-assembled and ready-to-use device so that upon receipt, assembly is avoided.

In an aspect, the base angle formed between the legs is between about 40° and 60°, such as about 50° to ensure adequate toe clearance during a patient's stride.

Any of the devices described herein may be further described in terms of the separation distance between the pole outer surface and the mast outer surface, such as a separation distance that is greater than or equal to 1 cm and less than or equal to 5 cm.

In another aspect, any of the mobility assistance devices provided herein comprise a mast having a bottom end and a top end; a base comprising a first base leg and a second base leg to form an open footprint such as an at least two-sided base footprint, wherein one end of each of the first and second base legs connect to the mast bottom end to form a vertex region, and the mast and base footprint form a mast angle having an acute angle so that the mast extends within a region that vertically extends from the two-sided base footprint. A first wheel is connected to the first base leg; a second wheel is connected to the second base leg, and a third wheel is connected to the vertex region, wherein each of the wheels are configured to stably contact a supporting surface on which the device rests. A height adjustable mobility handle is connected to the mast, wherein the height adjustable mobility handle translates along at least a longitudinal portion of the mast between the top end and the bottom end, wherein the mobility handle is configured to receive an applied force to stably ambulate the device over the supporting surface under the applied force. In an aspect, the mast longitudinal portion refers to about the upper portion of the mast, such as at least the upper 80%, upper 60% or upper 40% of the mast. In an aspect, the upper portion is about 60% of the upper portion of the mast so as to ensure the positioning of the mobility handle does not interfere with the function of the mounting arm that supports a medical component, such as a catheter bag, pleur-evac, or the like.

As described above, the mobility assistance device may further comprise a pole connected to a top portion of the mast and the bottom portion of the mast, wherein a central portion of the pole is separated from the mast by a separation distance. This central portion may be used to support a medical component, such as an infusion pump.

The mobility handle may further comprise a platform having a lip around an outer circumferential portion to support a material within an inner portion of the platform and prevent sliding of the material off the platform.

In the embodiment where the device is deployable, the system comprises a mast for holding one or more medical components (including via another element such as pole, mounting arm, or hooks attached thereto), and a base comprising a first base leg and a second base leg, wherein one end of each of the base legs is pivotally connected to the mast bottom end, wherein in a base-deployed configuration the mast forms an acute angle relative to the base and in a base-storage configuration each of the base legs and the relevant portion of or all of the mobility handle pivot to a position that is substantially parallel to the mast. The device is designed so that the mast angle and position relative to the base footprint ensures the mast is located over the base footprint, and preferably a central region of the base footprint.

Deployable refers to a device or respective element of the device that is capable of being positioned to provide a stable deployed (e.g., "folded-out") configuration and is also capable of being positioned to provide a compact stored (e.g., "folded-in", "collapsed") configuration. In an embodiment, in the base storage configuration each of the base legs, and optionally the grip handles and mounting arm, are positioned in a manner that is parallel to the mast. In this aspect, parallel encompasses paired surfaces that are within about 20° or within about 10° of parallel. In an embodiment the base legs are parallel to the mast but not touching the mast. In an embodiment the base legs are parallel to the mast and touching a mast surface in at least one axial location. In an embodiment, substantially the entire length of the base leg contacts a mast surface. In an embodiment, the collapsed or stored device has at least three or four wheels, that provide device motion over a support surface, wherein the stored device is parallel to the support surface. In this aspect of the stored configuration, the front wheels connected to the vertex region do not contact the support surface.

Any of the wheels provided herein may be on casters to provide swiveling. Any of the wheels may have a brake to prevent movement of the device. In an aspect, only the wheels connected to an end of the first and second base legs have brakes, including brakes that may be engaged or disengaged with a foot.

The mast of the present invention can have any of a variety of shapes, so long as the mast and base legs are capable of relatively compact storage when the base legs are positioned substantially parallel to the mast. Accordingly, the mast has an axial or longitudinal direction selected from the group consisting of angled, curved and linear. In an aspect the mast is angled or curved. An angled or curved mast is useful for positioning the IMS near objects such as a bed, gurney, tables and dressers, for example. In an aspect the mast is linear. A linear mast is the simplest geometry and can yield the most compact configuration suitable for wall-hanging storage, placement within a cart capable of holding a plurality of IMS devices of the present invention, or under shelves or beds.

Any of the systems described herein can be of any appropriate dimension or shape, so long as the device is stable and resistant to tipping even when relatively heavy components are attached to the device. For example, the mast can have at least a portion that is linear, with the linear portion having an angle relative to vertical. The angle relative to vertical is any suitable angle, including an angle selected from a range of between about 5° and about 25°, 10° and 15°, or about 12°, thereby ensuring the mast, and more particularly components supported by the mast, is positioned over a central portion of the base footprint. The vertical distance between the top and bottom ends of the mast can have a range selected to match the height of a user (e.g., child versus adult). For example, the vertical height (e.g., distance of top end from the floor) is selected from a range of between about 3' and 6', 4' and 5', or about 4.5'. The telescoping pole provides additional vertical height, such as a height selected from a range of between about 1' and 2', or about 18". Accordingly, the total vertical height of the mast plus telescoping support in an exemplified embodiment is about 7'. In an aspect, the ability to fit individuals of different height or capability is achieved by adjusting the mobility handle height to a desired vertical distance from the support surface (e.g., the floor). For example, an individual who requires vertical support may deploy the mobility handle to a lower vertical height so that the individual's arm strength may be exerted against the mobility handle to assist in movement. An individual not requiring such a vertical support, may position the mobility handle at a relatively higher vertical position.

The base footprint of the mobility assistance device with three wheels contacting the support surface is generally triangular, with each vertex corresponding to the contact point between the wheel and supporting surface. For embodiments having two front wheels the front vertex point actually corresponds to a straight line of length corresponding to the wheels separation distance. The particular mast and base leg geometry are dependent on each other so that the deployed device is extremely stable. In an embodiment, the base legs have a length selected from a range of between about 2' to 3.5', 30" to 36", or about 3'. The base footprint corresponds to about the area between the base legs and for base legs of 36" length and vertex angle of 70° is about 610 in$^2$. In an aspect, where there are two front wheels connected to the vertex region, the footprint is a truncated triangle or a trapezoidal region having a base footprint area selected from a range that is greater than 500 in$^2$ and less than about 600 in$^2$, or about 555 in$^2$.

In another aspect, any of the systems described and claimed have a base vertex angle selected from the range of 40° to 100°, 35° to 75°, or about 50°, where the base vertex angle is defined by the angle formed by the directions of the first and second base legs, and particularly the directions of the base leg ends adjacent to the mast bottom. An important aspect of the invention is that even for a device having a large base footprint and capable of holding a significant number of components, when not in use the device is capable of folding into a compact configuration having dimensions that are only slightly greater than the dimensions of the mast when in an upright stored configuration. For example, when folded for storage, the footprint of the device can be as small as the horizontal cross-section of the mast, or about the cross-section of the mast plus the cross-sections of each of the base legs in their stored position. In contrast, the footprint of the deployed IMS corresponds to the area defined by the deployed base legs and corresponding volume also including the mast height. Accordingly, in an aspect the stored footprint is less than 30%, less than 20%, or less than 5% the deployed footprint. In an aspect, the deployed and stored volume may be used to characterize the compactness of the system. In an aspect, the stored system has a stored volume that is less than about 5500 in$^3$, such as about 5250 in³ or less. Similarly, any of the devices provided herein relate to a deployed volume and stored volume, wherein the stored volume is less than or equal to about 30%, 20%, or about 15%, of the deployed device, including a device having a pole-deployed or a pole stored configuration. In an aspect, the stored volume is about 5250 in³ or less, and the deployed volume is greater than or equal to about 26,640 in³ (pole stored) or 44,440 in³ (pole deployed) corresponding to a stored volume that is 20% or 12% that of the deployed volume. The special configuration of the pole holders at the top of the pole further minimizes the stored volume by ensuring holders are confined to the region that faces toward the base footprint behind the mast and not in the front of the mast. One convenient aspect is that the stored and deployed configurations are readily interchanged without having to remove any parts or pieces. Therefore, the device can be deployed or stored by a single person in a rapid, reliable, and convenient manner.

In another aspect, any of the devices provided herein comprise an oxygen tank holder for securably holding an oxygen tank, such as an upper tank holder connected to the mast for coupling with an upper portion of an oxygen tank and a lower tank holder connected to the first or the second base leg for coupling with a base portion of an oxygen tank.

The upper oxygen tank holder optionally comprises an arm for securing an oxygen tank at an oxygen tank axial location, such as an arm that is a clasp. In an embodiment, the arm is a loop having an internal passage configured to receive an oxygen tank at an axially-defined circumferential contact region, such as a loop that is connected to the trunk.

In an embodiment, the loop is rotationally positionable relative to the first and second base legs to receive an oxygen tank over the first base leg or the second base leg. In this manner, added oxygen tank stability is obtained on either side of the device.

Any of the devices provided herein may have a lower tank holder comprising a receiving surface and a circumferential lip for receiving a bottom surface of an oxygen tank.

In an embodiment, the device may comprise a pair of lower tank holders, such as a second lower tank holder, wherein a first lower tank holder is connected to the first base leg and the second lower tank holder is connected to the second base leg. This is convenient when matched with a rotatable upper tank holder so that the oxygen tank may be held on either side of the device, as desired. Alternatively, the lower tank holder may be reversibly connected to the first base leg or the second base leg, so that an oxygen tank is supported by the first base leg or the second base leg by moving the lower oxygen tank holder between base legs.

In an aspect, any of the devices provided herein further comprise an oxygen tank, wherein the oxygen tank is in an upright position and supported by the first base leg or the second base leg. Any sized oxygen tank that is considered portable for a patient may be used. For example, the oxygen tank may be a D cylinder (4.38" diameter and 16.5" height) or an E cylinder (4.38" diameter and 25.5" height).

The oxygen tank holder is configured to secure an oxygen tank to a longitudinally-defined portion of the first or second base leg arm, the longitudinally-defined portion extending from the mast to about half of the base leg arm length. In an aspect, the position is fixed and determined by the geometry and position of the top tank holder relative to the underlying base leg. Alternatively, the position is adjustable such as by positioning the bottom tank holder on the base leg at different distances from the mast.

Any of the devices provided herein may comprise an upper oxygen tank holder connected to the mast by a mounting arm, wherein the upper oxygen tank holder is rotably connected to the mounting arm. In this manner, the upper oxygen tank holder is indirectly connected to the mast via an intervening element, such as the mounting arm.

In another embodiment, any of the devices provided herein further comprise an outlet strip mount connected to the pole, mast, base legs, or other portion, for securably receiving an outlet strip. In an aspect, the mount is connected to the pole, such as by a rotational and translational connection. The outlet strip may have a plurality of electrical sockets to power a plurality of electrical devices. The outlet strip may have an electrical cord for connecting to a source of power, such as an electrical socket (e.g., wall, floor, etc.) or a battery that is supported by the mobility assistance device. The outlet strip mount may comprise a top bracket configured to connect to one end of an outlet strip; and a bottom bracket configured to connect to a second end of an outlet strip, wherein the outlet strip second end is opposed to the outlet strip first end. In this manner, the outlet strip may "click into" the space between the brackets and the brackets may be subsequently rotationally adjusted and/or translationally (e.g., height) adjusted to obtain desired positioning of the outlet strip. Accordingly, the top bracket, the bottom bracket, or both the top and bottom brackets are adjustable vertically and rotationally to independently position an outlet strip in any vertical and rotational position with respect to the pole.

The top bracket and the bottom bracket may be nestable with respect to each other to provide a bracket stored configuration when no outlet strip is connected to the top bracket or the bottom bracket. Nestable refers to a surface of the bracket that is shaped to mate with the surface of another bracket, thereby maximizing available space on the pole when an outlet strip is not needed.

Any of the devices provided herein optionally comprise an outlet strip connected to the outlet strip mount. Optionally, the outlet strip is reversibly connected to the outlet strip mount so that the outlet strip is removed as desired.

Any of the devices provided herein optionally further comprise a first cord management bracket and a second cord management bracket, each of the cord management brackets connected to the mast and separated from each other by a separation distance, wherein the brackets are configured to receive a cord in a wrapped configuration and reliably secure a wrapped cord to a longitudinal portion of a mast surface. In an aspect, the cord management brackets comprise articulating brackets that move from a stored position where the bracket is generally aligned parallel to the mast surface to a deployed position configured to receive and store an electrical cord.

BRIEF DESCRIPTION OF THE DRAWINGS

FIG. 25: Rear view of the mobility assistance device of FIG. 23, with certain components in a stored configuration.

FIG. 26: Mobility assistance device in a fully stored configuration and upright ready for storage in an upright configuration.

FIG. 36A is a close-up view of the accessory module and engagement mechanism for deploying/storing the mounting arm. FIG. 36B shows the mounting arm in a deployed configuration. FIG. 36C shows the mounting arm in a stored configuration.

DETAILED DESCRIPTION OF THE INVENTION

Figure 1A:
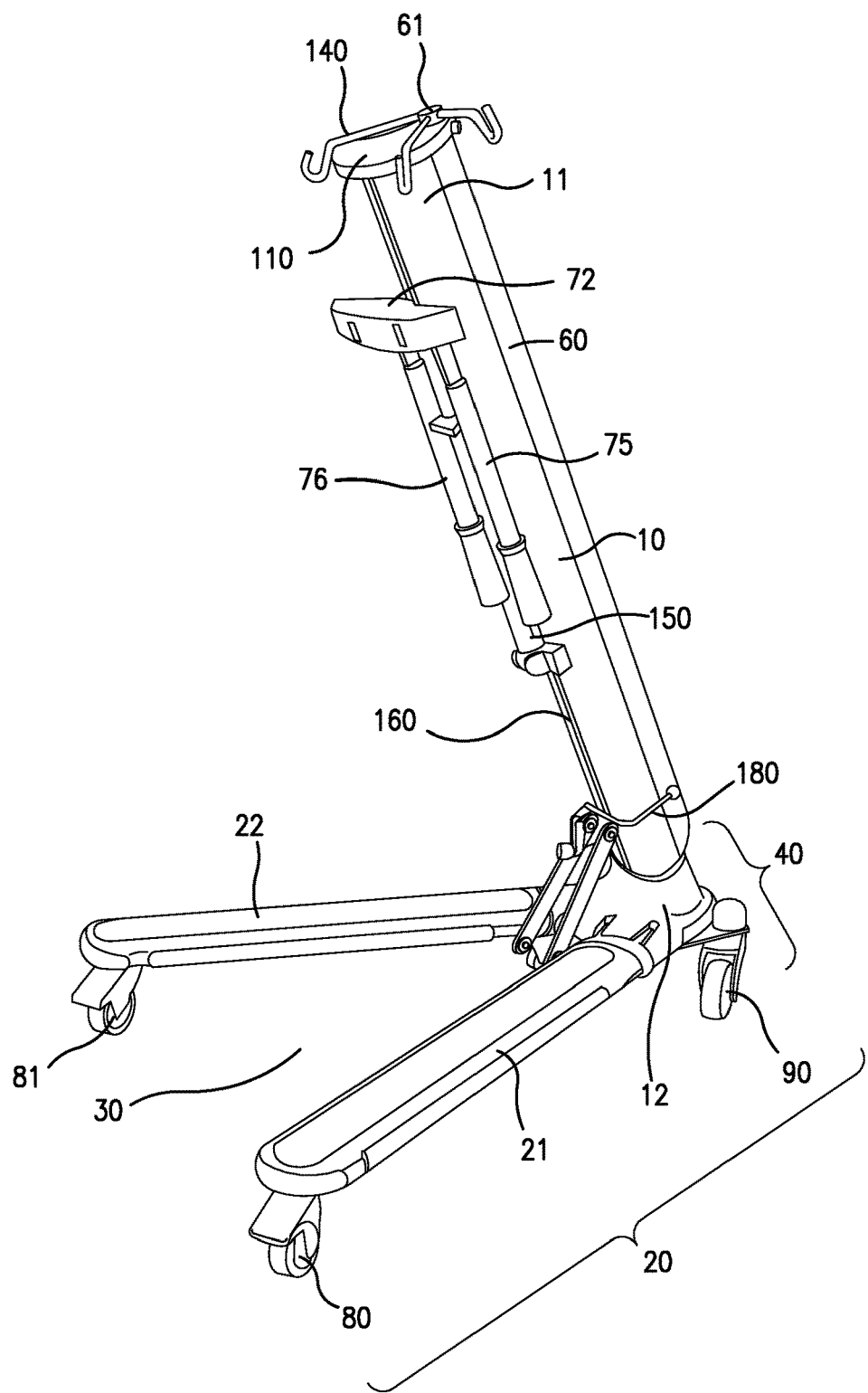
FIG. 1A: View of the mobility assistance device with base deployed. The grip handles for receiving a force from a patient are in a stored position. The pole is not extended. 1B: Side schematic diagram of the device illustrating the mast angle, θ, formed by the angle between the mast and the base. Φ shows a corresponding angle with respect to vertical. 1C: Side schematic diagram showing an embodiment where the axial mast has separate angled portions, with one mast portion vertical and another portion tilted with respect to vertical. 1D: Schematic illustration of the two-sided base footprint defined by the two base legs meeting at the vertex region, for the aspect where there are a pair of wheels connected to the mast bottom, along with notional lines. 1E: Schematic illustration of the mast and pole axis, along with the separation distance between the pole and mast outer surface. 1F: Schematic illustration of pole and mast in a substantially non-parallel configuration, with the pole vertical with respect to the base footprint and positioned within a region that vertically extends from the base footprint.

Referring to the drawings, like numerals indicate like elements and the same number appearing in more than one drawing refers to the same element. In addition, hereinafter, the following definitions apply:

The invention is broadly a mobile intravenous (IV) pole or mobility assistance device capable of supporting one or more components to which a user is connected. The base footprint combined with the angled mast that forms an acute angle with the base footprint allows for a patient to ambulate without interference from any of the base legs, mast, or components connected to the system. The mast angle shown in the exemplary embodiment creates stability for hanging a large number of heavy devices and/or materials to the system while maintaining their ability to connect or interface with the patient.

"Mast" refers to the central shaft or pole to which any number of components (e.g., medical components) can be held or attached. The mast has at least a portion that is angled to form an acute angle with the base footprint thereby providing enhanced stability to the device, even when multiple relatively heavy components are attached to the device and the device is ambulated by a user. In an aspect, the mast is linear (e.g., not bent or curved) and extends over a region having an outer limit defined by a vertical extension of the base footprint so that the mast is positioned over the base footprint. The invention encompasses other mast shapes such as bent and/or curved masts, so long as at least a portion of the mast is angled with respect to horizontal such that components held by the device are positioned substantially over the base footprint, thereby ensuring maximum stability and resistance to tipping. In an aspect, the mast top end is positioned over a central portion of the base footprint, such as over a middle portion of a centerline relative to the base footprint, including a middle portion that is centered within 30%, 20%, 10% of the base footprint center, or at the base footprint center.

"Base" refers to the portion of the system that rests on a supporting surface (e.g., a floor). In the exemplified embodiment, the base comprises a pair of base legs with each base leg pivotally connected to the mast bottom end. "Pivotally connected" refers to a base that is deployable with respect to the mast. Accordingly, when the base legs are folded-out the legs are positioned at an angle relative to the mast and the system is ready for supporting one or more medical components. When the base legs are folded in they are positioned substantially parallel to the mast and the device is relatively compact and ready for storage. As used herein, "parallel" refers to a longitudinal direction of the base leg being within at least 5° of true parallel with respect to the longitudinal direction of the mast. "Substantially parallel" refers to the longitudinal directions of the axis or the surfaces being within at least 30°, at least 15°, or at least 5° off parallel.

Many features of the device are said to be deployable. "Deployable" refers to the component being "folded in" or "stored" (positioned) to make the component or device more compact for storage, or "folded out" or "deployed" (positioned) to make the component or device ready for use.

In the embodiment where the mast is a straight shaft, the base legs can have correspondingly straight geometry, with the base legs forming a base leg apex angle corresponding to the vertex located at the mast where each of the legs are pivotally connected. In the embodiment where the mast is angled or curved, each of the base legs are preferably correspondingly angled or curved to ensure maximum compact storage of the device when the base legs are pivoted to a position parallel to the mast. Although it is preferred, for maximum compactness, that the base legs and mast have similar longitudinal geometry, the invention tolerates mismatch in geometry without undue loss in the ability to compact the device when not in use.

The contact points between the base and the surface on which the base rests define the edges of a base footprint. "Base footprint" refers to the area defined by the contact points between the base and the supporting surface and a notional line running from the base leg ends that are not attached to the mast. When three wheels are deployed, this area is triangular. When four wheels are deployed, this base area footprint is referred herein as trapezoidal. Base footprint may also refer to a shape corresponding to the base legs rather than the wheels contact points, so the base footprint shape may be triangular or trapezoidal (e.g., each of the base legs are linear with two front wheels separated from each other by a separation distance to provide a notional straight-line between the third and fourth wheels), or can have a more complex shape, with each side having a shape corresponding to a non-linear base leg, and a third notional straight-line that joins the base legs ends that are not attached to the mast. The base footprints provided herein are described as "open" in that the one end of the base footprint is open (e.g., no base leg or other elements) to accommodate a user and the area is sufficiently large to accommodate and not interfere with a user's stride during the user's ambulation of the device.

An aspect of the present invention is a mobility assistance device capable of ambulating over a supporting surface. "Ambulating" refers to a device that can move over a surface, and particularly a device capable of functioning as a walker for a patient that is connected to one or more medical components. In addition to the device functioning as a walker, the device is also constructed to ensure medical support personnel can readily maneuver the device that is deployed or stored and optionally connected to one or more medical components. "Medical component" refers to a material, device, or structure useful in providing medical treatment to a patient including, but not limited, bags of fluid such as intravenous (IV) fluid, infusion pump, pleur-evac, optical sources, power supplies, oxygen monitor, oxygen canisters, etc.

"Holding" or "attaching" a medical component to the device encompasses passive hanging (e.g., a bag suspended by a holder), orienting the holders to more securely receive the component, shaping the hanger to provide relief and recess features to facilitate secure holding as well as more complex connections such as a male-female connection with an adaptor connected to the devices (e.g., threaded screws, one-handed quick connects, snap-beads, etc.). Optional accessories such as light sources, calculator, computer, video screens, power supplies can be more permanently attached to and/or in the mast surface, or connected to other elements of the device, such as a pole or mounting arm, and/or supported by a platform.

The core device (e.g., mast and base legs) itself can be made from any of a number of materials including, but not limited to, traditional chrome, any metal or metal composites, fiberglass, plastics, carbon fiber, and/or composite material.

The device preferably has rounded edges and corners to minimize the chance of injury arising from inadvertent contact with the device. In addition, the device can be designed to be aesthetically pleasing, having dramatic sweeping legs with striking color, sharp and clean lines to reassure patients who are uncertain about ambulating. Accordingly, the vertex region may be formed from large and smooth surfaces that can provide accessible surfaces that can be readily cleaned and maintained and that minimize and spread impact force due to inadvertent contact of the vertex region with walls, doors, other devices or other persons.

EXAMPLE 1

Mobility Assistance Device with Extendible Pole

Figure 1B:
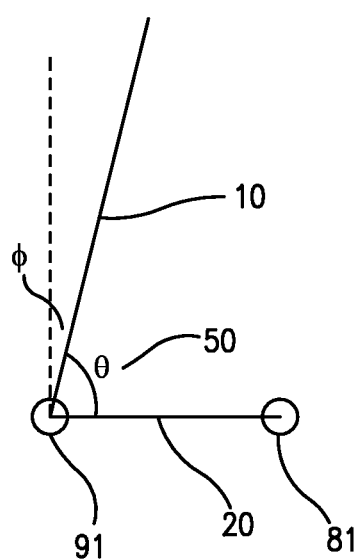

The mobility assistance device ("device") in its most basic configuration comprises a mast 10 connected to a base 20 and having a pole 60 positioned along the mast 10 surface. (FIG. 1A). The pole may be extendible. FIGS. 1-5 show a device in a base deployed configuration. The base 20 has a base first leg 21 and second leg 22 connected to the mast bottom end 12. The mast 10 forms a mast angle 50, a non-zero angle (Φ) relative to vertical and an acute angle (θ) relative to the base 20, as schematically illustrated in FIG. 1B.

Figure 2:
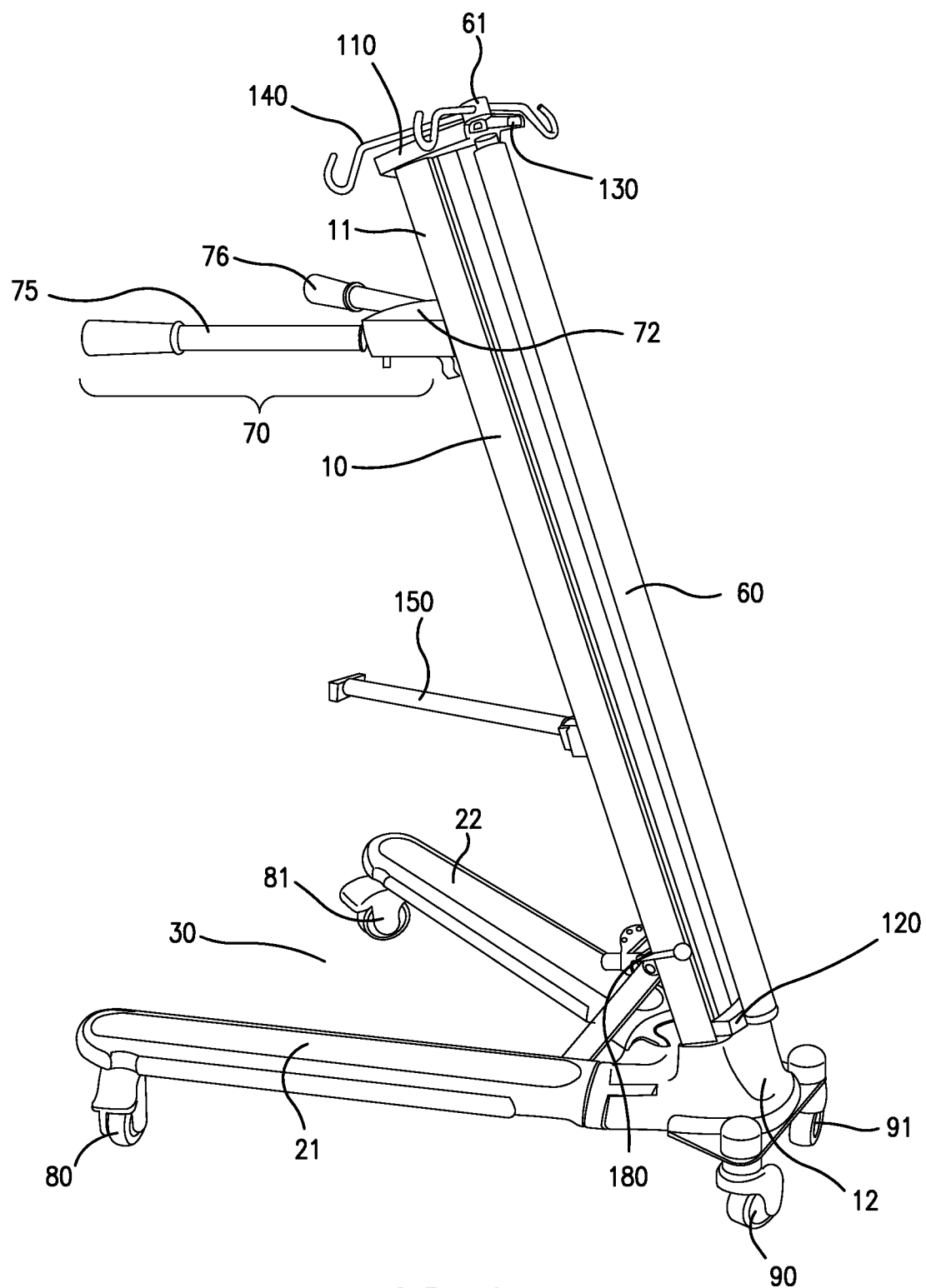
FIG. 2: View of a deployed device, with the base legs, mounting arm, and mobility handles deployed.
Figure 3:
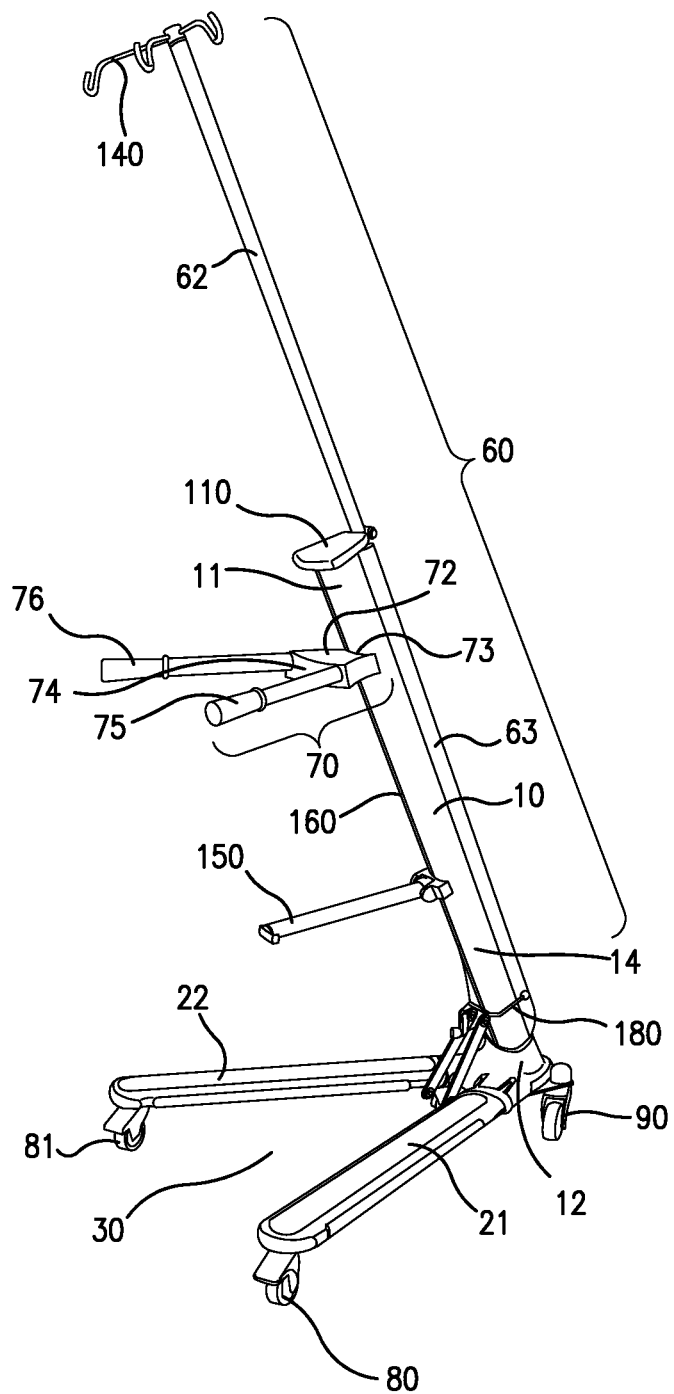
FIG. 3: View of the deployed device with the pole fully extended.
Figure 10:
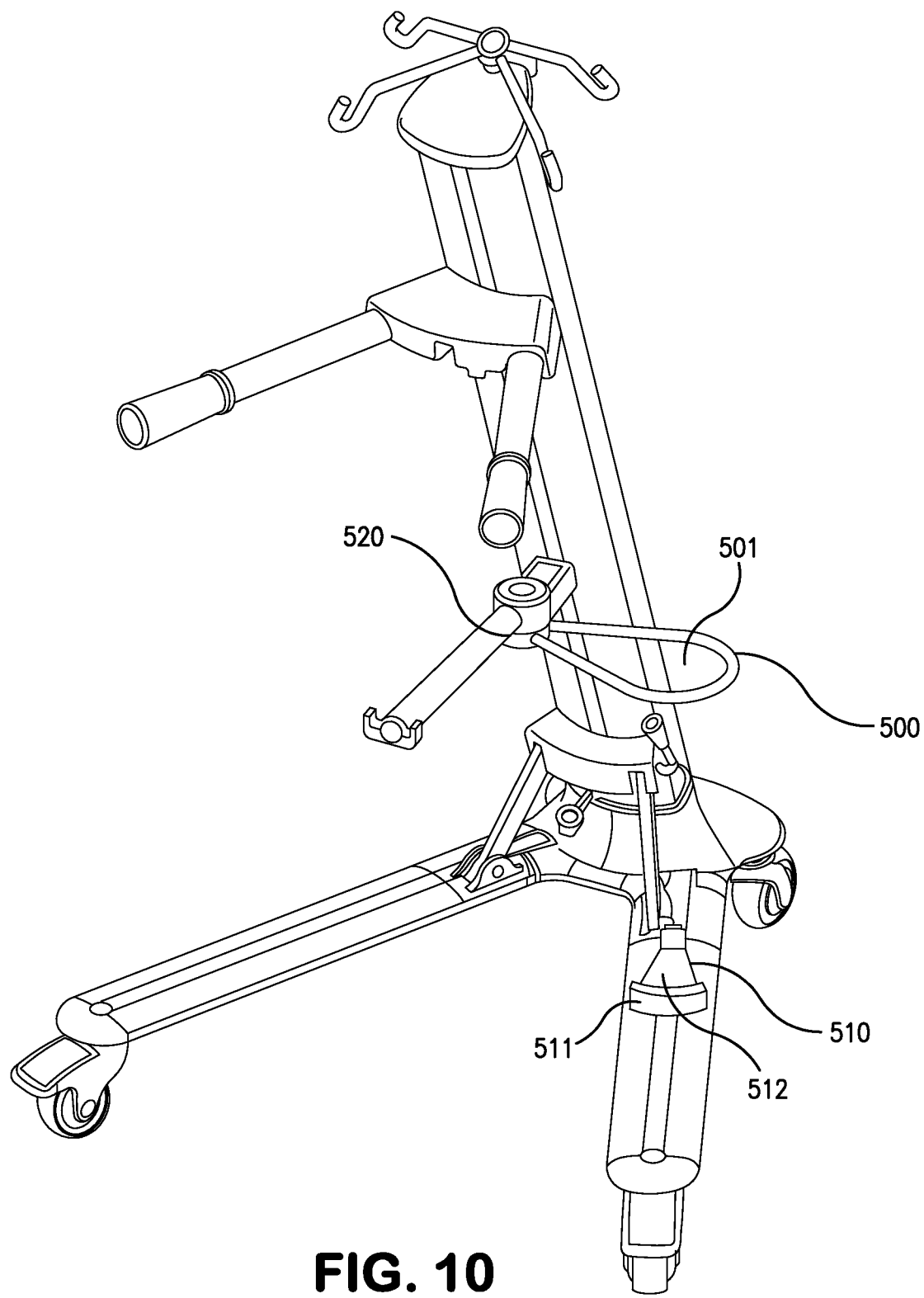
FIGS. 10-17: Various views of a mobility assistance device having an oxygen tank holder for securing oxygen tanks.
Figure 11:
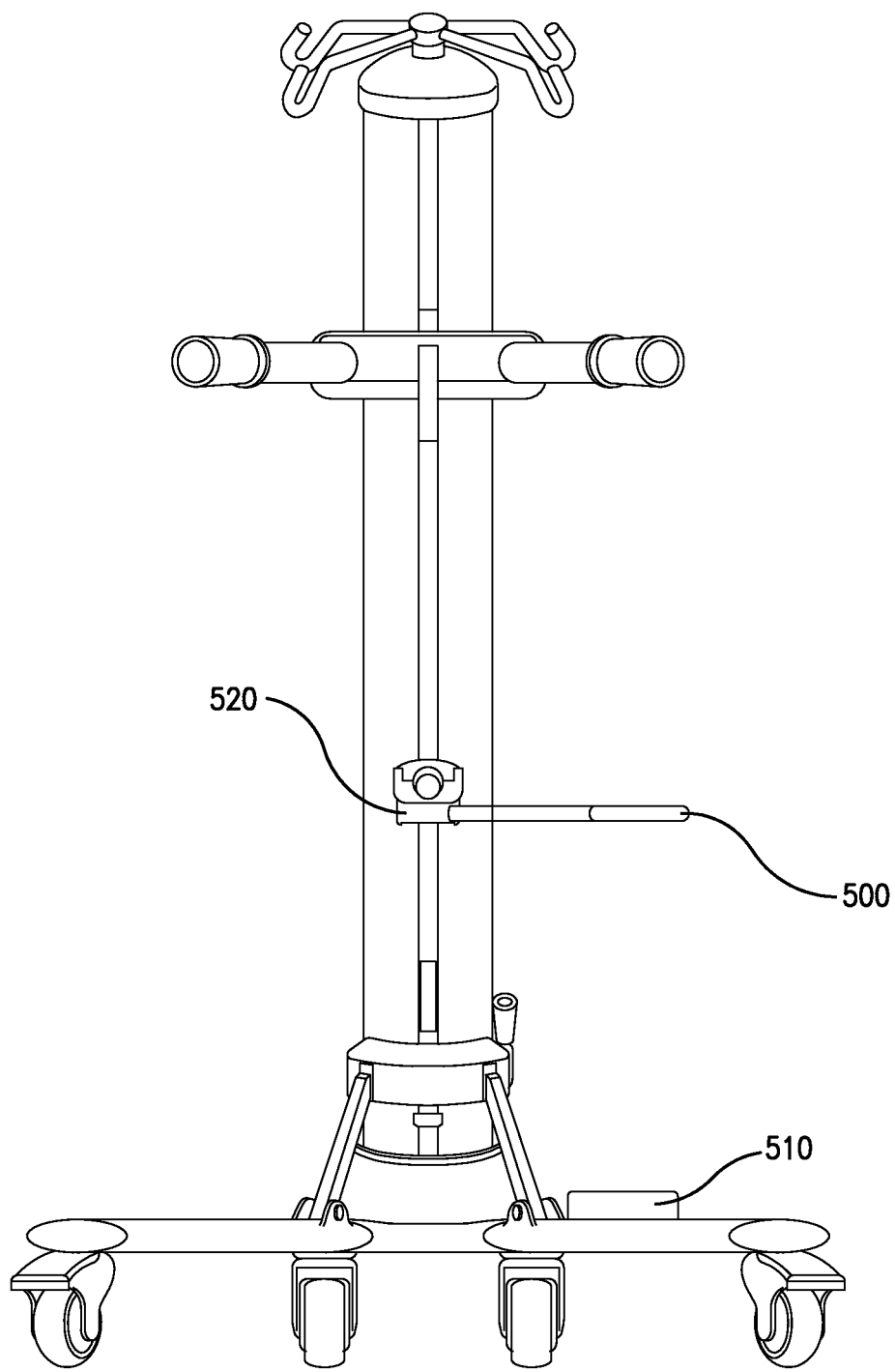
Figure 12:
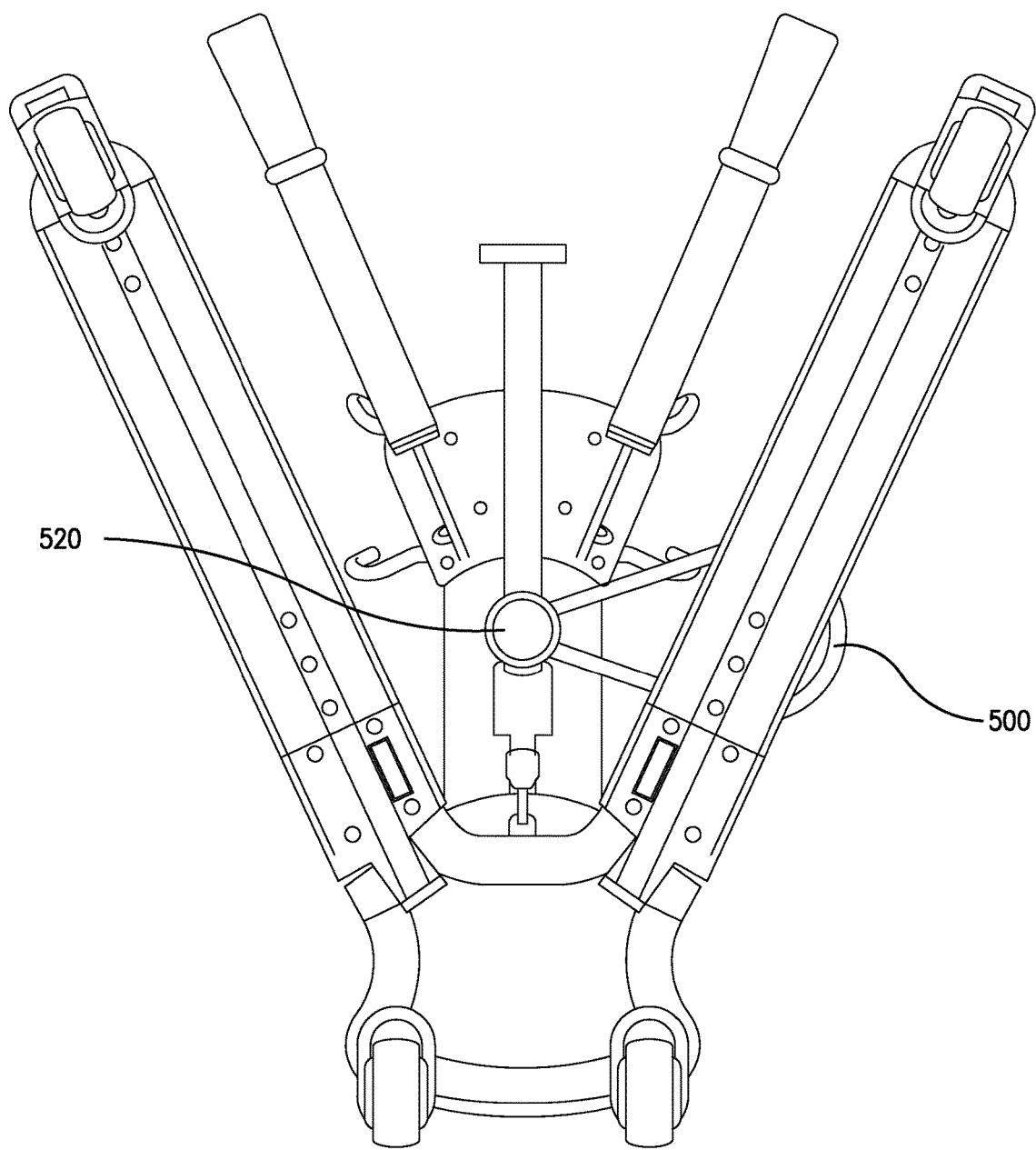

First wheel 80 and second wheel 81 are attached to base legs 21 and 22, and third wheel 90 and fourth wheel 91 are attached to the mast bottom end 12 at a vertex region 40 to form a two-sided base footprint 30 (FIGS. 1A, 10 and 2). The two sides of the base footprint 30 correspond to the base legs 21 and 22. FIG. 10. The device can have one wheel attached to the mast bottom end 12. The exemplified embodiment illustrates two wheels 90 and 91 attached to the mast bottom end 12 in the vertex region 40 and are separated by a separation distance (92), such as between 5 cm and 50 cm. Accordingly, two-sided base footprint refers to a footprint that may have three sides to provide an open trapezoidal base footprint, but two of the sides are considered major sides that are significantly longer than any third side that is at the vertex region for embodiments when there are four wheels that ambulate the deployed device over a support surface. This geometry is also referred to as a "truncated triangle". The added fourth wheel at the vertex region provides additional control and maneuverability of the device. Any of the wheels may be independently brakeable to ensure the device does not move. In an embodiment, one or both of the first and second wheels have a brake mechanism. In an embodiment, one or both of the third and fourth wheels have a brake mechanism.

Referring to FIG. 10 the mast can extend over the base footprint centerline 200 and end in a region that corresponds to a central portion 201 of the centerline and centered in or around the base footprint. This is also referred herein as the mast that extends within a region that vertically extends from the base footprint 30. This may be quantifiably described in terms of being within a defined central portion of the centerline, such as the middle third region. Of course, the robust geometrical design of the device provides tolerance to the positioning of the end of the mast along centerline 200. For example, the end of the mast may extend to the last third of the centerline, so long as there is not interference with patient ambulation or sight-line. Accordingly, the mast length and base angle are selected such that in a base-deployed configuration the position of the mast top end (Pos.) along the centerline having a length of $L_{centerline}$ may be defined as $0.331L_{centerline} < \text{Pos.} < L_{centerline}$, or $0.331L_{centerline} < \text{Pos.} < 0.71L_{centerline}$. Optionally, at least a portion of the mobility handle is positioned above the base footprint centerline, such as the mobility handle symmetry centerline that corresponds to, but is vertically above, the base footprint centerline. Preferably, the height of the mast is less than eye level of a patient so as to provide good line-of-sight during use of the device by an ambulating patient.

The device encompasses non-linear base leg shapes including, but not limited to, curved, U-shaped, multiply-edged. For maximum compact storage (e.g. see FIG. 7), the shape of the mast is preferably complementary to the shape of the base legs, ensuring parallel positioning of the base legs 21 and 22 to the mast 10 when the base legs are rotated closed.

Figure 1C:
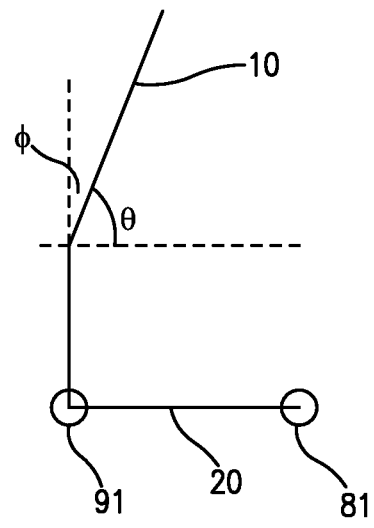
Figure 1D:
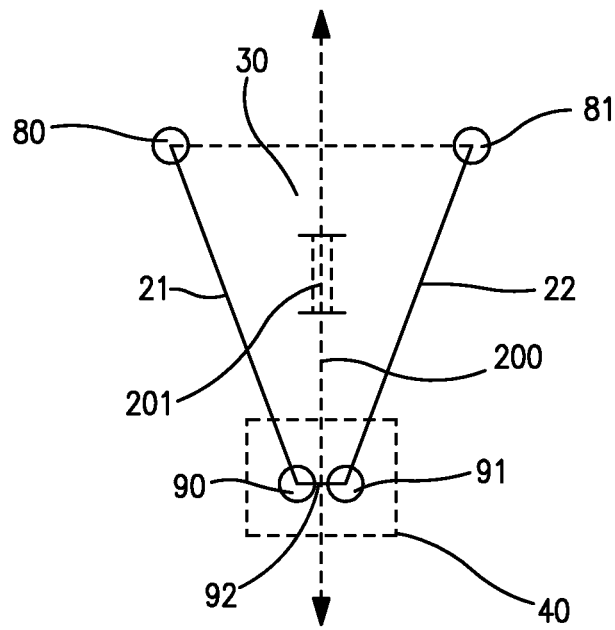

The mast 10, similar to the base legs 21 and 22, can also be non-linear. The invention encompasses a mast 10 that is curved or comprises more than one mast section with each selection having a unique angle with respect to horizontal. For example, the mast can have a bottom section that is vertical, (e.g., 90° angle with respect to horizontal) and an upper section that is angled with respect to horizontal, as illustrated in FIG. 1C.

The base footprint 30 and mast angle 50 ensure that the center of gravity, even with one or more relatively heavy components attached to the system, is confined to a region within the base footprint. Such a configuration ensures a deployed device remains stable and tip-resistant even when it is ambulating and/or supporting a heavy load. Greater stability is provided by positioning mobility handle 70 over a region of base footprint 30. In the exemplified embodiment, the mast angle 50 is 70°. The mast can have any axial shape/direction, so long as a significant portion of any suspended component is over the base footprint, thereby ensuring maximum stability and resistance to tipping.

Figure 4:
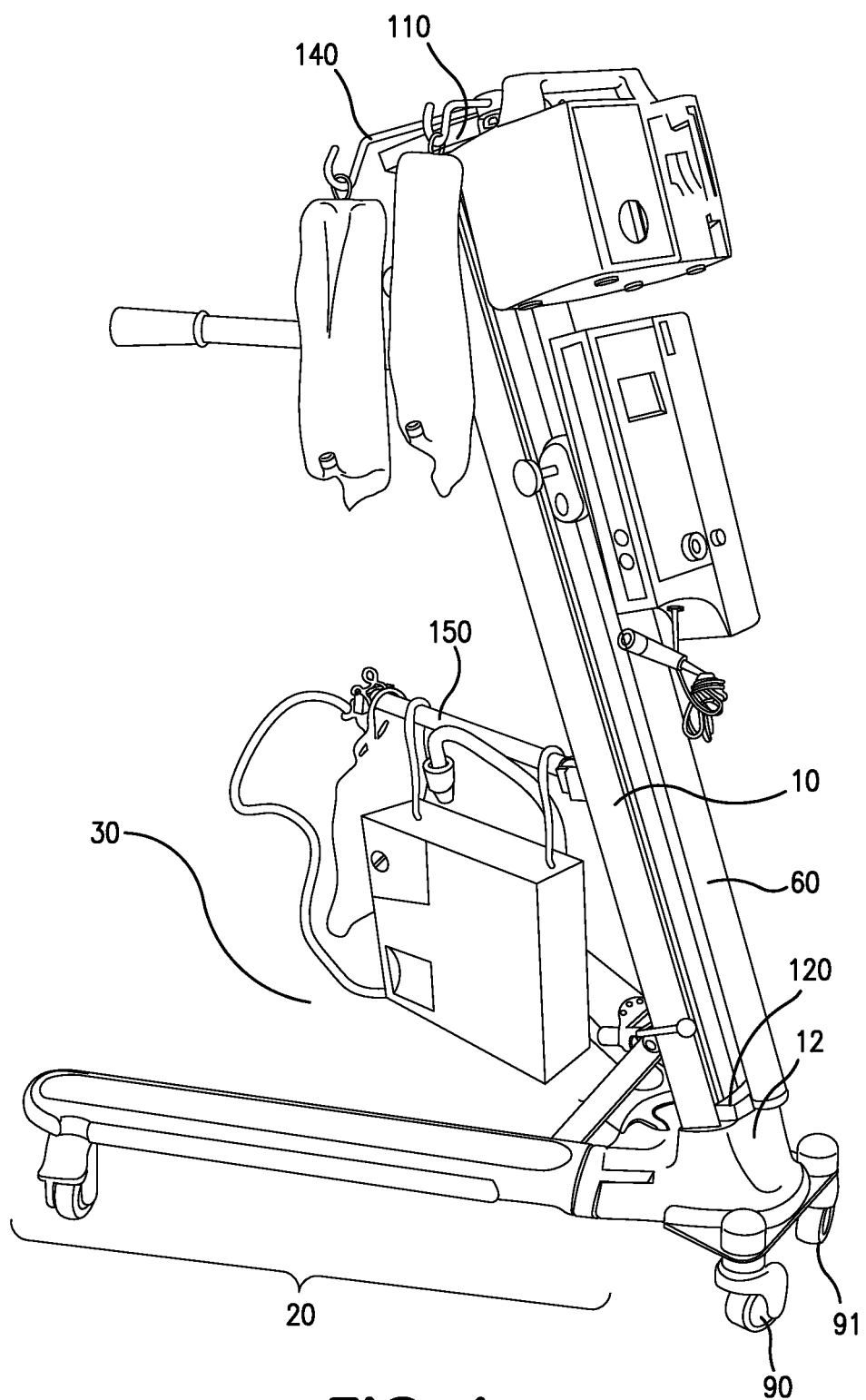
FIG. 4: View of the device with medical components attached to the mounting arm, holders, and pole. The pole is not extended.
Figure 5:
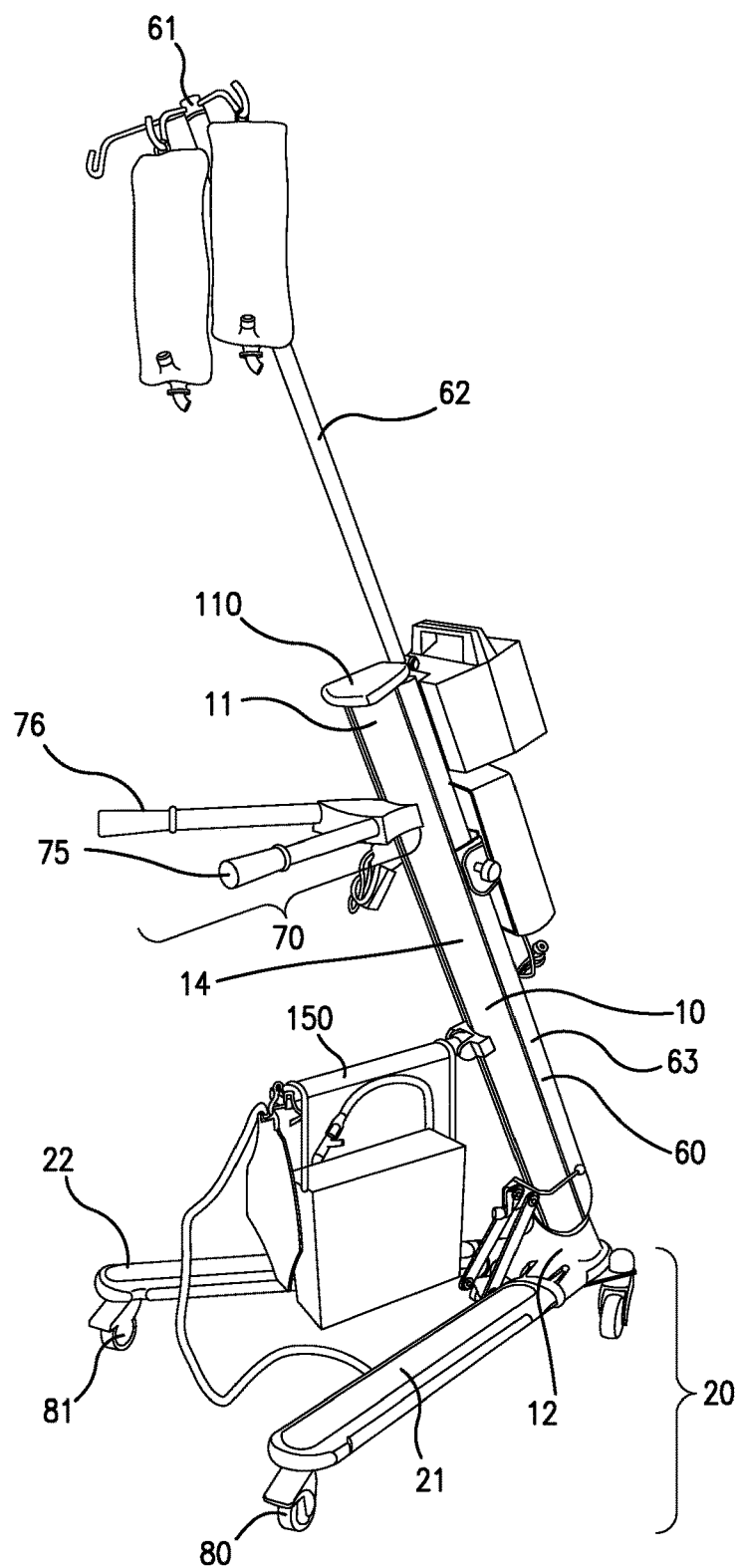
FIG. 5: View of the device shown in FIG. 4 with the pole fully extended.
Figure 6:
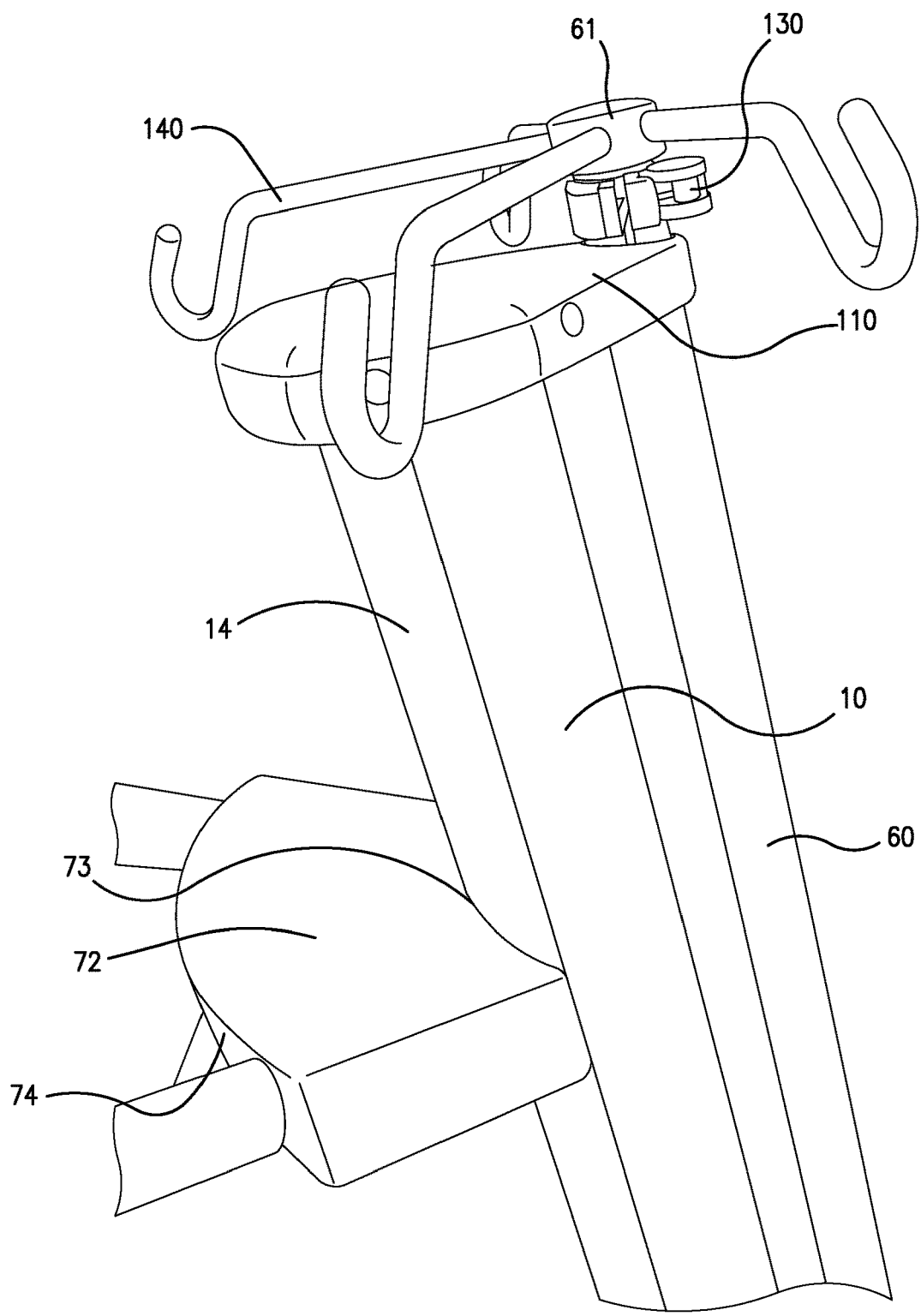
FIG. 6: Close-up view of the upper portion of the device including the mobility handle platform, the holders at the top of the pole, and a quick release clamp for adjusting the pole length.

The device is configured to receive several medical components, as exemplified in FIGS. 4 and 5, showing the combination of medical components and deployed device supporting medical components. One means of receiving medical components is a pole 60, including a pole that may be extended (compare FIG. 2 and FIG. 3). The pole 60 is connected to a top connector 110 at the mast top end 11 and a bottom connector 120 located near the mast bottom end 12, and can extend telescopingly during use between a fully extended configuration (FIG. 3) and a stored pole position (FIG. 2). "Telescopingly" as known in the art (see, e.g. U.S. Pat. Nos. 5,458,305; 4,905,944) refers to the height of an object being adjustable by entering another object thereby adjusting the height. The pole itself can support several devices (see, e.g. FIG. 4), such as IV fluid bags and infusion pumps connected to hooks/holders at the pole top and/or directly to the pole central portion. In the exemplified embodiment, the pole upper portion 62 is height adjusted by mating with the pole lower portion 63, and the height of the entire pole 60 is adjusted by releasing and engaging a quick release clamp 130 (FIGS. 2 and 6). The device may employ any means of adjusting the height of the pole, such as via adjustable pins, or connectable upper poles of different lengths.

The pole 60 can connect to one or more than one holders 140 (see, e.g., FIGS. 1A and 6). The holders are particularly useful for supporting medical fluid bags, such as IV fluid bags. In an embodiment, four holders 140 are configured such that the first and second holder are extendibly opposed to each other in a left and right direction relative to the device, and the other two are evenly rotationally spaced in an inward-facing direction (see FIGS. 1A and 6). The invention comprises means for selectably adjusting the location of the holders. Means for selectably adjusting the holders encompasses relatively simple configurations such as female receptacles spaced around the surface of the pole top end 61 for receiving a holder or hook having a complementary male configuration. The receiving means can be by a threaded screw, snap bead, or other system known in the art. In an aspect, the holders are configured such that they all face towards the user and no holders are positioned past the front of the pole. This ensures the collapsed volume is minimized and facilitates compact storage for shipping and avoids undue voids within a container in which the collapsed device is stored.

Figure 1E:
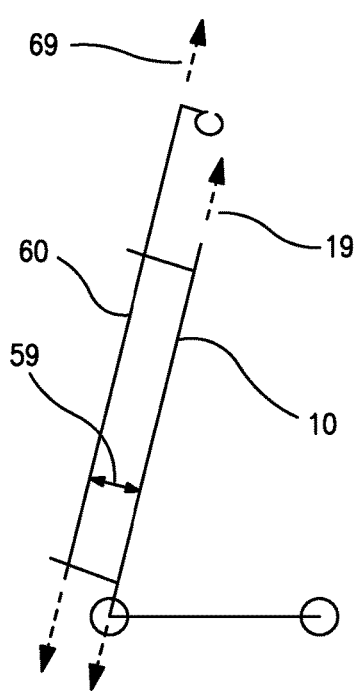
Figure 1F:
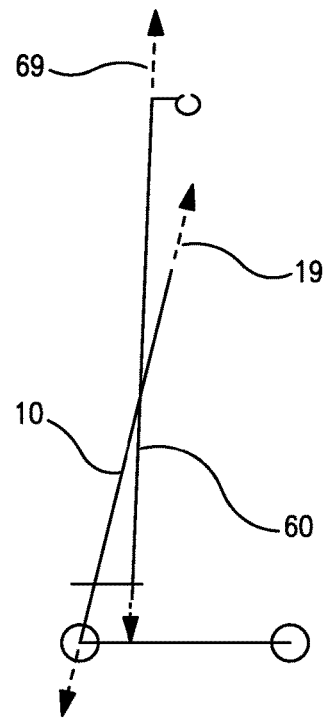

The longitudinal axis 69 of the pole 60 is separated from the outer surface of the mast 10 by a separation distance 59, such as a separation distance that is greater than 0 cm and less than 10 cm. In the exemplified embodiment the longitudinal axis of the pole 60 is aligned parallel to the longitudinal axis 19 of the mast 10 (FIG. 1E). The pole longitudinal axis 69 can be non-parallel with respect to the mast longitudinal axis 19, as long as the device remains stable when medical components are added (FIG. 1F). The separation distance is important and is selected so as to accommodate and reliably support a medical component such as an infusion pump (see, e.g., FIGS. 4-5). An advantage of the devices provided herein, is that the angled geometry and separation distance 59 allows for off-vertical positioning of the infusion pump along any portion of the pole, which conveniently positions the control face of the infusion pump for a medical caregiver for monitoring, accessing and controlling even during device ambulation.

EXAMPLE 2

Height-Adjustable Mobility Handle

Figure 8:
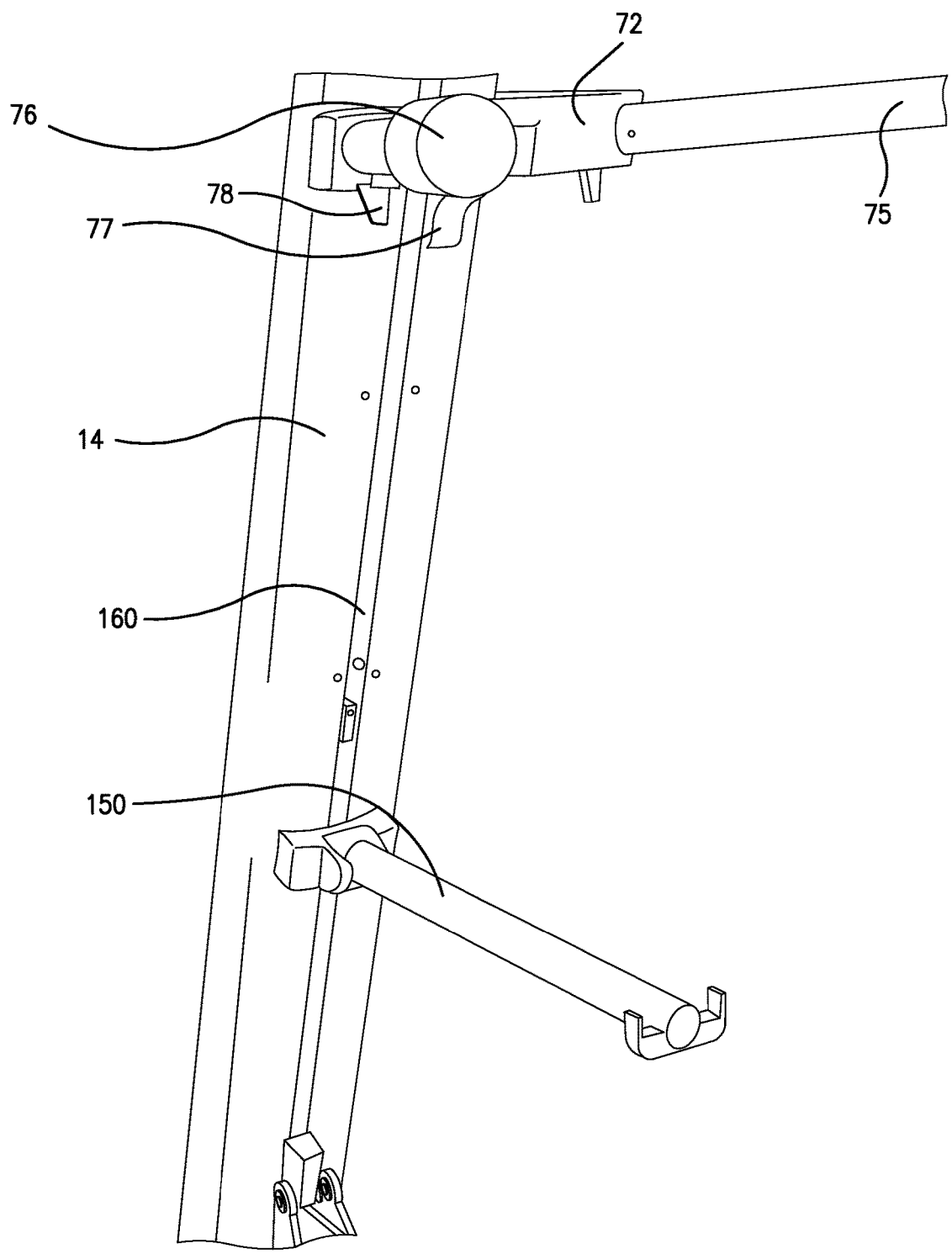
FIG. 8: Close-up view of the middle portion of the device, showing the translational connection between the mobility handle and mast along with a quick release cam for height positioning of the mobility handle and engagement mechanism for rotation of grip handles into a stored or deployed configurations.
Figure 29:
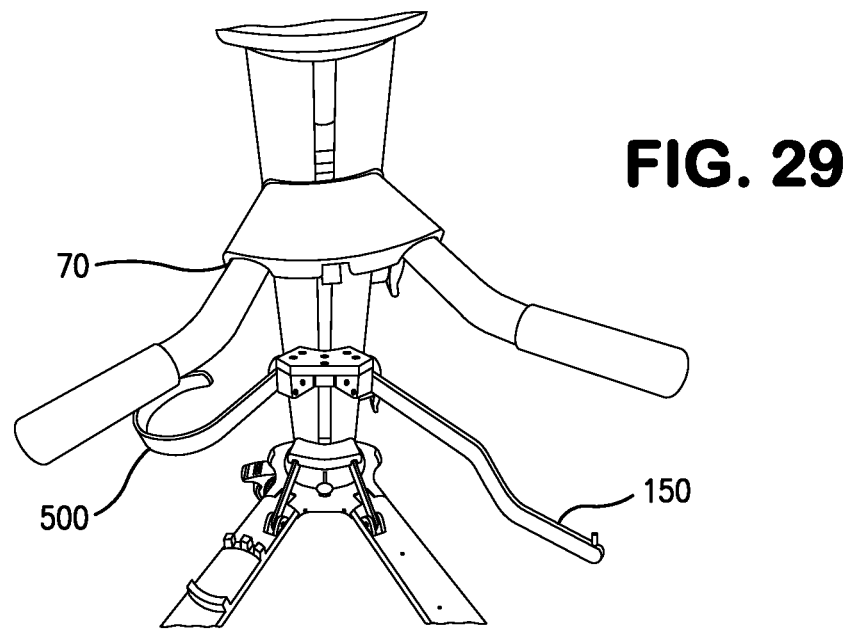
FIG. 29: Close up view of the shaped handle configuration with the oxygen canister holder and mounting arm in a deployed configuration.

A useful embodiment of the invention is a system that has a mobility handle 70 that comprises a platform 72, and a first and second grip handle 75 and 76 (FIGS. 2-6). In this aspect, the mobility handle is height adjustable, but along a handle plane that is substantially parallel or parallel to the base footprint. In this aspect, the mobility handle 70 that is height adjustable can be by a number of mechanisms. In the exemplified embodiment, the mobility handle first platform end 73 engages with a groove 160 in the inward-facing surface 14 of the mast 10, for height adjustability along the mast (FIGS. 6 and 8). The first and second grip handles 75 and 76 engage the second platform end 74, where they may pivot or rotate downward into a stored position by engagement mechanism 78 and may be height-adjustable by quick release cam 77 mechanism (FIGS. 1 and 8). Alternatively, the grip handles can be moved into a storage position telescopingly or by other mechanisms, or they can be removed. Engagement mechanism 77 for handle rotation or height adjustment may be implemented as a button on the side of the handle bracket to engage handle rotation. In the exemplified embodiment, the grip handles 75 and 76 extend from the platform 72 along a plane that is substantially parallel to the base plane defined by the first and second base legs 21 and 22. The grip handles can be positioned along other planes. For example, they can extend straight rearward over the base footprint or have other shapes, such as a swept-out configuration (FIG. 29). The platform 72 can have a lip around its perimeter or at the platform second end 74 for holding a tray or other components, and is a particular user-friendly feature for the user or caregiver for reliably holding personal items in a safe and convenient manner (e.g., cell phones, wallets, identification, charts, food, cups and cupholders).

EXAMPLE 3

Mounting Arm

The embodiment illustrates a rotable mounting arm 150 connected to the mast inward-facing surface 14 for holding additional medical devices and other relatively heavy objects (e.g. small platforms, power supplies, pleur-evac etc.). FIGS. 2-5 show the mounting arm 150 in its deployed position. The mobility assistance device can be used with the mounting arm in its stored configuration (FIG. 1A).

EXAMPLE 4

Storage Configuration

Figure 7:
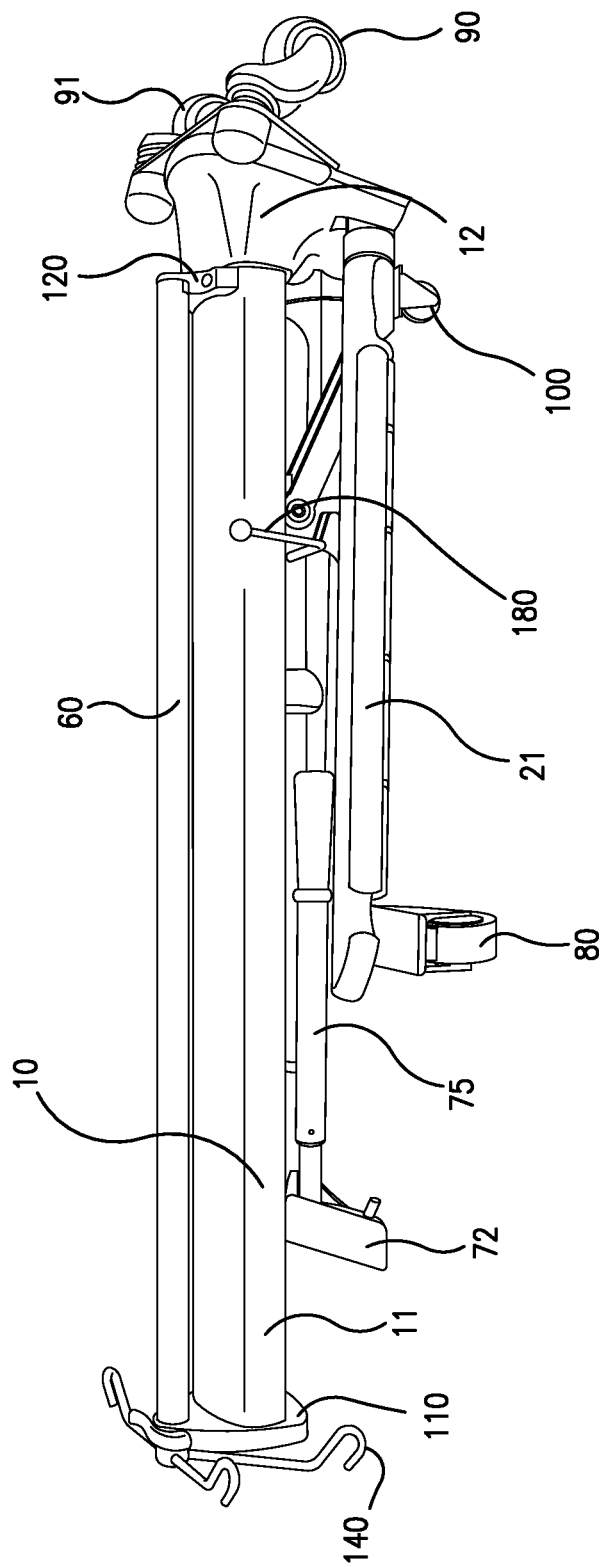
FIG. 7: View of the device in the stored configuration.
Figure 9:
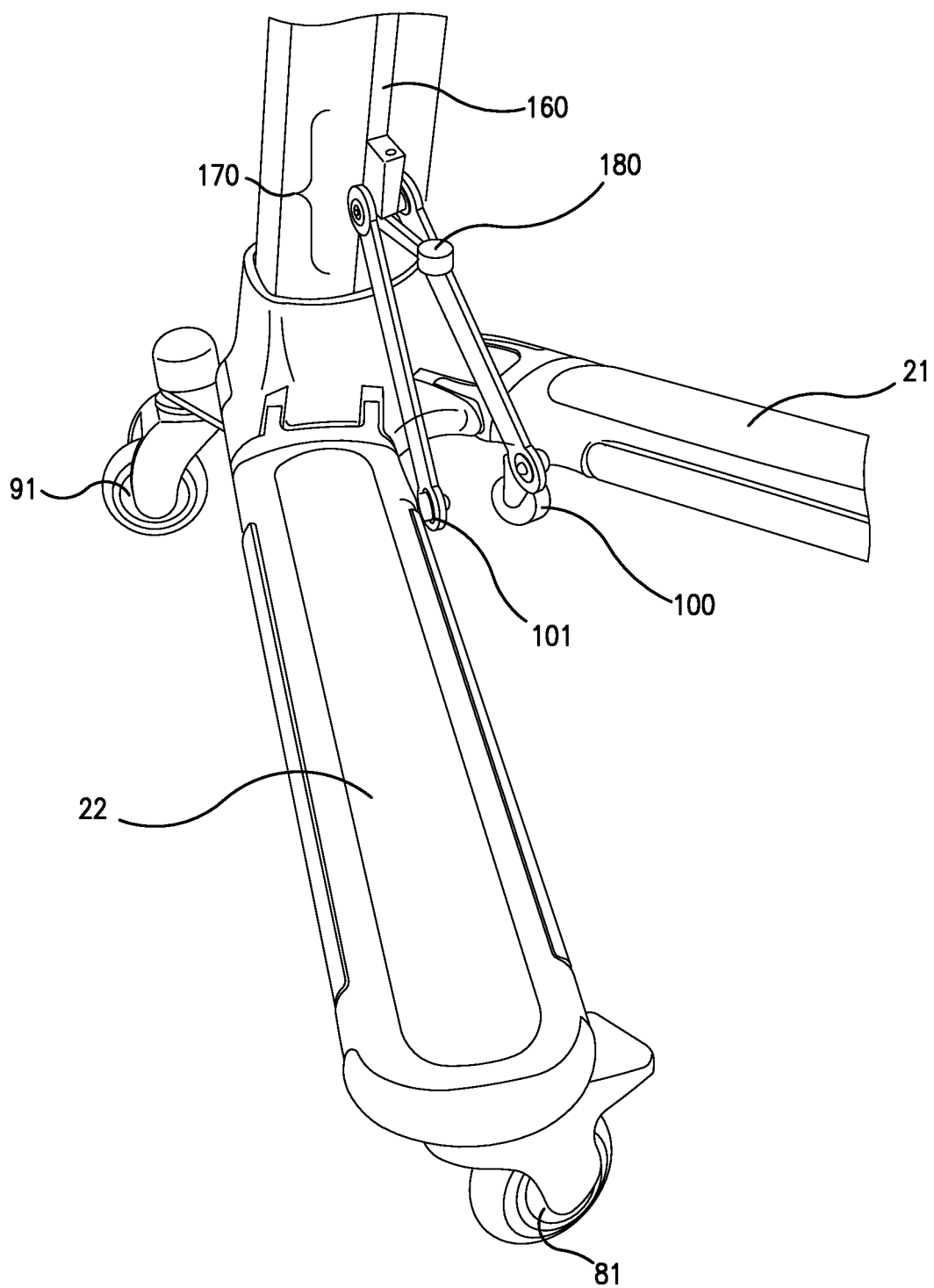
FIG. 9: Close-up view showing the vertex region, the rotational connection between the base legs and mast, and the fifth and sixth wheels connected to the base legs.

FIG. 7 illustrates the device in its fully stored configuration. In particular, each of the individually deployable components (base legs 21 and 22, grip handles 75 and 76, mounting arm 150, pole 60) are stored to provide maximum compactness. Optional fifth and sixth wheels 100 and 101 (FIG. 9) assist in moving the device by rolling it over a surface to or from a storage location or to an area where it is to be deployed. In this aspect, the device is readily moved in a stored configuration, including by application from a foot, by the contact with the floor of the first, second, fifth and sixth wheels, with the wheel connected to the vertex region (fourth and fifth wheels) not in contact with the support surface. Alternatively, as described above the fifth and sixth wheels may be trolley wheels that rollably engage with a support surface when the mast in the device stored configuration is tilted relative to the support surface. In this manner, a caregiver may reliably move the stored device by simply lifting a top portion of the mast. During device deployment the fifth and sixth wheels, in contrast, do not touch the support surface (see, e.g., FIGS. 1-2). Alternatively, the fifth and sixth wheels are replaced with glides to facilitate sliding over the support surface. The base legs 21 and 22 are easily stored by one person by engaging a safety lever 180. The safety lever incorporates a gas spring and mechanism 170 for gentle and reliable storage and deployment. The gas spring is operably connected to a base leg deployment mechanism that rotably connects the base legs to the mast, including in an "over-center" configuration.

The device is able to be compactly stored, while retaining the ability to be quickly and easily deployed by a single person. For example, pressing the safety lever 180 and applying a deployment force sufficient to overcome the over-center force from a gas-spring allows base legs 21 and 22 to unlock from their stored position (parallel to the mast 10). The grip handles 75 and 76 are rotatably unlocked by mechanism 78 (FIG. 8) or 3410 (FIG. 34) for storage and height-adjusted by quick release cam 77. The handles may be manually lifted into the deployed configuration (parallel to the base 20) and locked in place with manual force. A ball spring plunger-type device can hold the handles in the stored position. A pull on the handle of the device, with no lock to release, can deploy the handle. The mounting arm 150 is manually rotated upward into a stored configuration (parallel to the mast 10) and downward into a deployed configuration (parallel to the base 20), or can be stored via other mechanisms known in the art, including but not limited to a quick release cam, pins, screws, locks, etc. In the exemplified embodiment, the storage volume of the device is less than or equal to 50" by 10.5" by 10". The invention encompasses dimensions that yield a larger storage volume.

EXAMPLE 5

Mobility Assistance Device with Oxygen Holding Capability

In an embodiment, any of the mobility assistance devices provided herein includes a means for securing an oxygen tank. This is an important embodiment because many patients, including patients connected to an IV infusion or other medical component, also require oxygen. Without a safe, reliable and easy to use mechanism, it would be difficult for such patients to ambulate. Accordingly, an aspect of the invention is an oxygen tank holder that reliably secures an oxygen tank to the mobility assistance device. In an embodiment, the holder is positioned so as to not interfere with mobility assistance device function, including stable movement and ability to compactly store. Accordingly, the holder may be connected to one of the base legs or the mast. The holder may connect to the bottom of the oxygen tank, the top of the oxygen tank, and/or somewhere between the top and bottom ends of the oxygen tank. The oxygen tank holder may comprise a plurality of distinct components, with one component holding one portion of an oxygen tank and another component holding a different portion of the tank.

One example of an oxygen tank holder is provided in FIGS. 10-17. In this example, the oxygen tank holder comprises multi-components, an upper tank holder 500 and a lower tank holder 510. The upper tank holder may be an arm that couples an upper portion of the oxygen tank and the lower tank holder shaped to couple with a bottom portion of the oxygen tank. "Couples" refers to a connection between the oxygen tank and mobility assistance device that is reversible yet reliably secure. This facilitates swap out of oxygen tanks and ease of use by a medical caregiver or even the patient who receives oxygen from the oxygen tank.

"Arm" refers to the ability to circumferentially secure an oxygen tank. In an aspect, the arm partially encloses around the circumference of the oxygen tank, such as by a clasp that receives the oxygen tank. Alternatively, as depicted in FIG. 10, the arm may be a loop with an internal passage 501 so that an oxygen tank may be placed in the internal passage with the bottom resting on a base leg. Optionally, the upper tank holder is rotationally positionable relative to the base, so that the oxygen tank bottom is supported by the first base leg or the second base leg, as desired. The rotational may be at the trunk or another location, such as the mounting arm via a rotational connection 520.

For additional support, such as to ensure the bottom of the oxygen tank does not slide off the base leg, a lower tank holder 510 may be connected to, or formed from, a base leg. For example, the base leg may be formed to receive an oxygen tank in a hollowed-out portion. Alternatively, and as shown in FIGS. 10-17, the lower tank holder may be connected to a base leg and have a receiving surface 512 and a circumferential lip 511 to ensure the bottom surface of the oxygen tank is secured to and supported by the base leg. The lower tank holder may connect to either base leg, such as by being interchangeably removable or by providing a lower tank holder on each base leg. In an aspect, the oxygen tank holds breathable oxygen or medical grade oxygen. Typical tanks include D or E tanks, having diameters of about 4 to 5 inches (e.g., 4.38 inches) and heights of about 16 to 26 inches (e.g., 16.5 inches or 25.5 inches). As desired, other size tanks may be accommodated with correspondingly sized holders.

Figure 13:
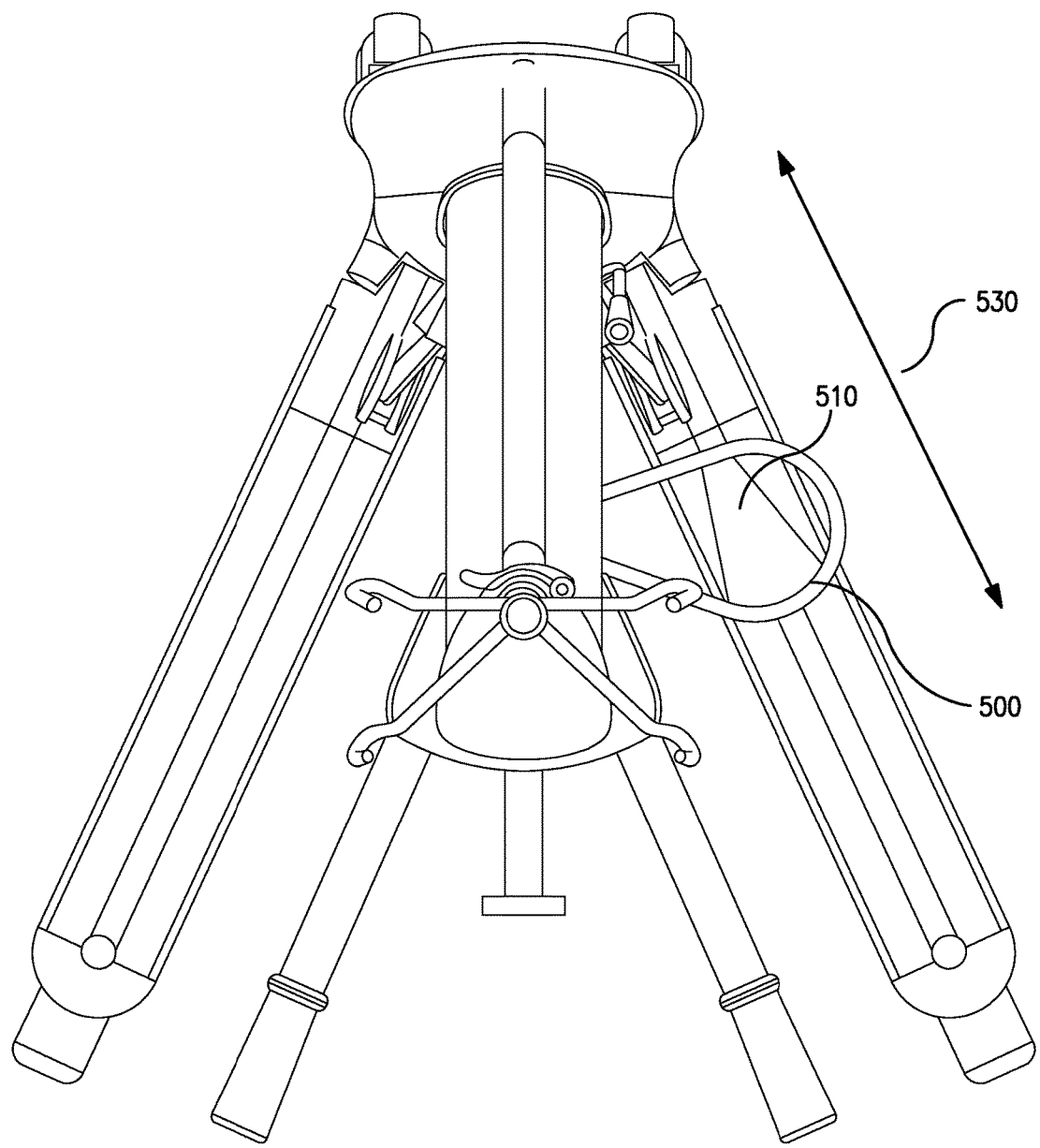
Figure 14:
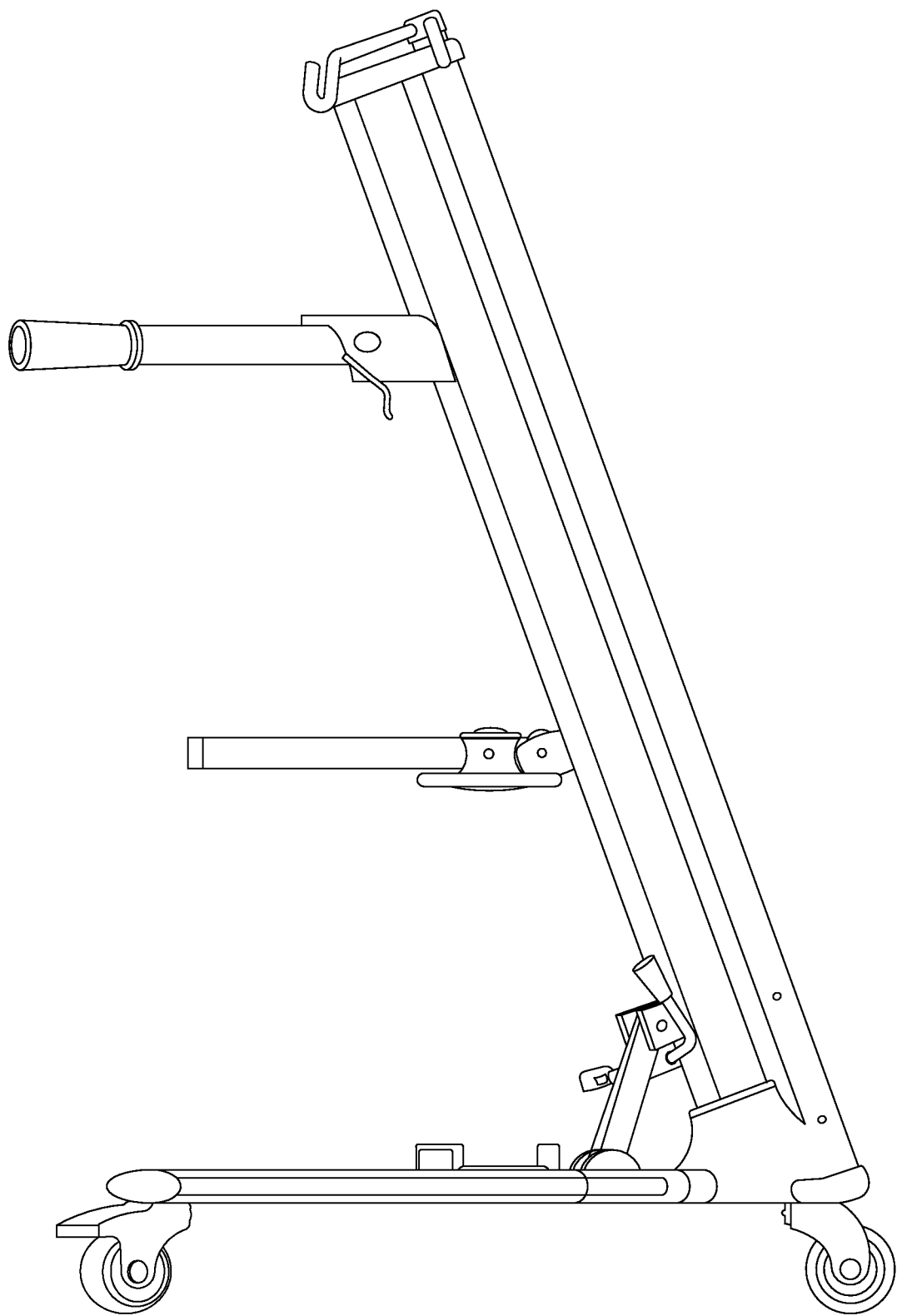
Figure 15:
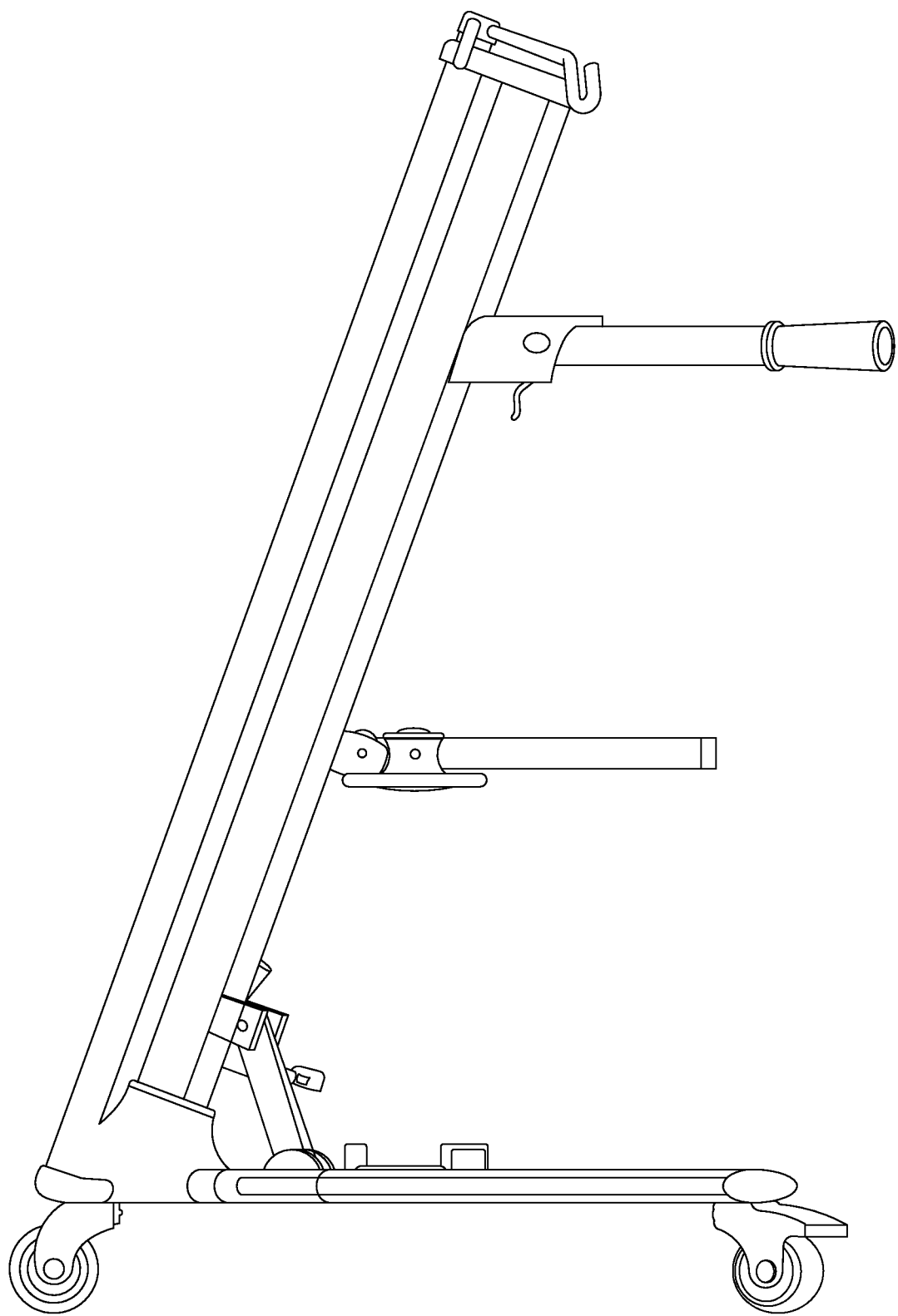
Figure 16:
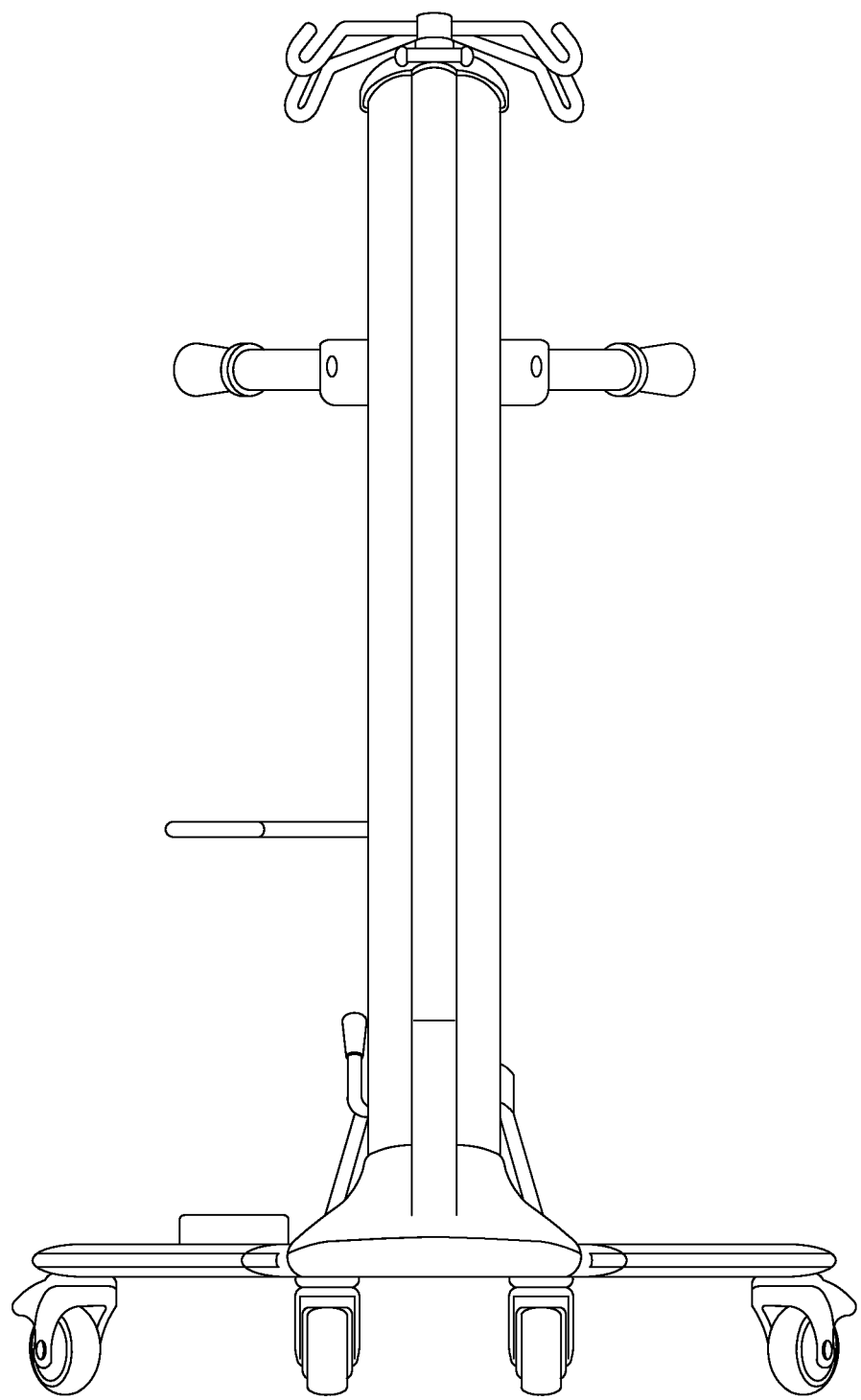
Figure 17:
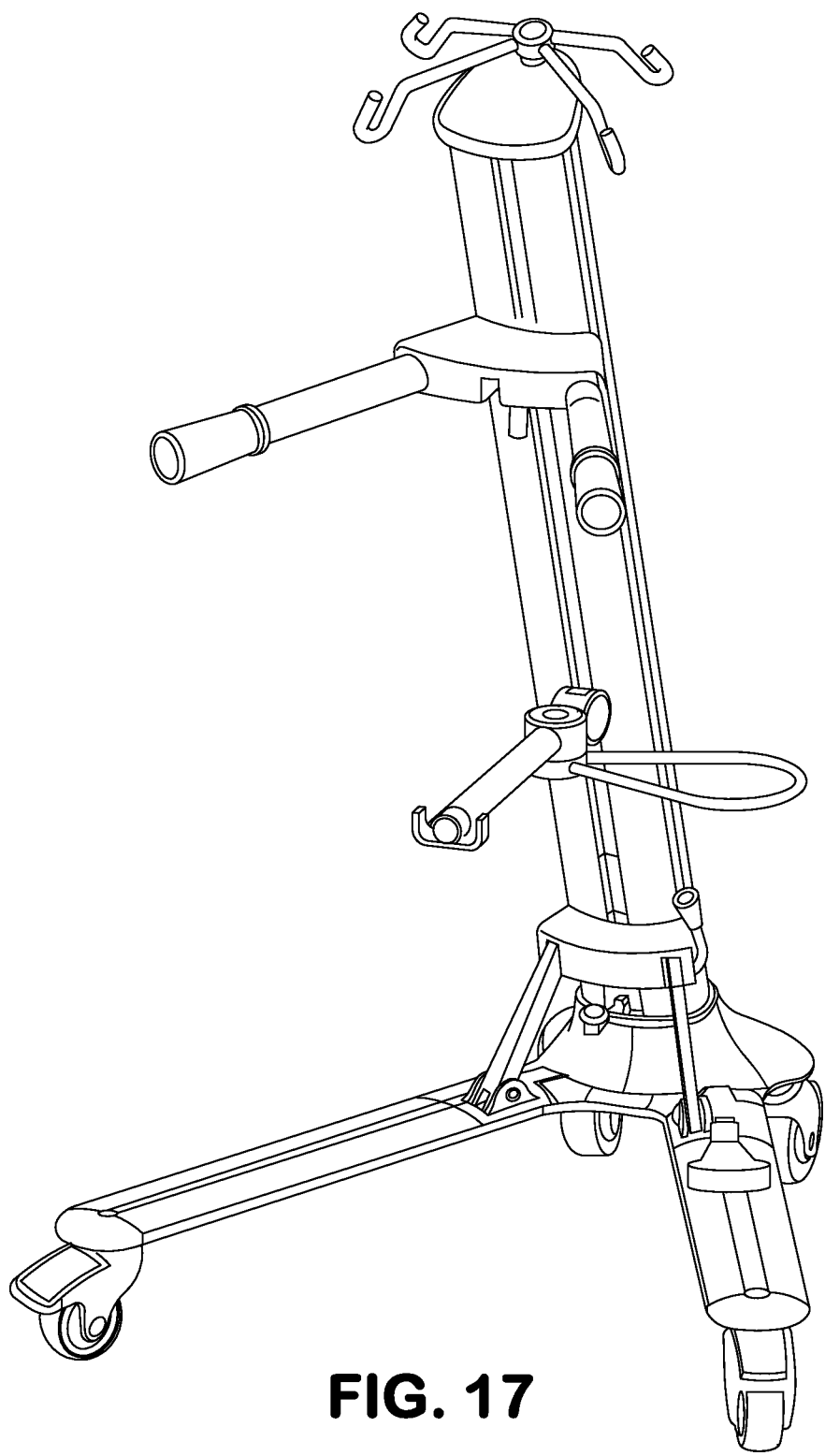

FIG. 13 is a top-view illustrating the upper tank holder 500 and lower tank holder 510. This view illustrates that oxygen tanks can be efficiently and reliably supported by the system. Furthermore, oxygen tanks can be readily mounted and readily removed, in a safe and easy manner, such as by vertically inserting/removing through the internal passage 501 of the upper tank holder 500 and resting on lower tank holder 510. The particular point of support of the oxygen tank on the base leg (first or second base leg) may be selected as desired, such as over a longitudinally-defined portion 530 of the first or second base leg arm. In an embodiment, the longitudinally-defined portion may extend from the mast to about half of the base leg arm length, or any portion thereof, such as between about 10% and 40% of the base leg length as measured from the mast.

EXAMPLE 6

Power Management

Figure 20:
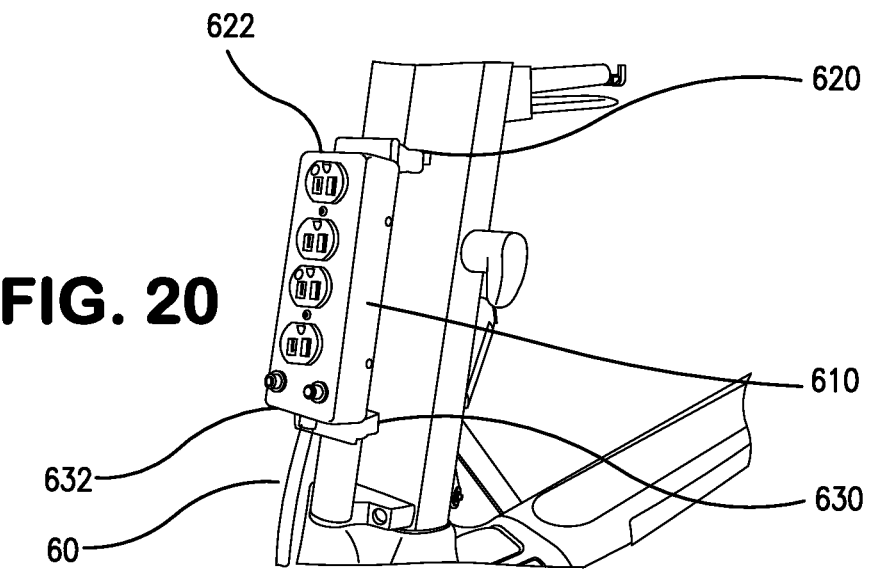
FIG. 20: Photograph of a power outlet strip connected to the mobility assistance device.
Figure 21:
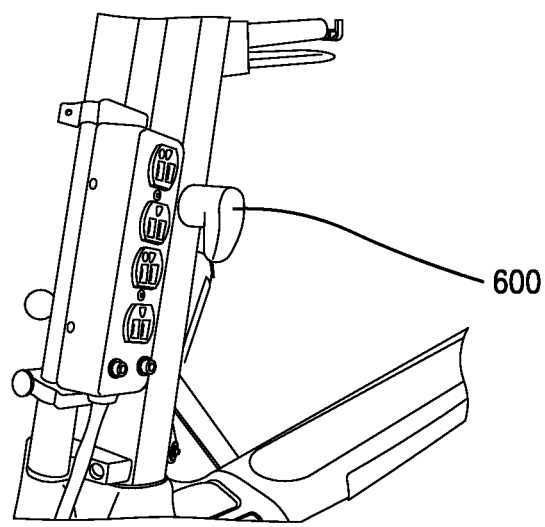
FIG. 21: Photograph indicating the outlet strip brackets are rotatably connected to the mobility assistance device, so that the power outlet strip may be oriented in any desired direction.
Figure 22:
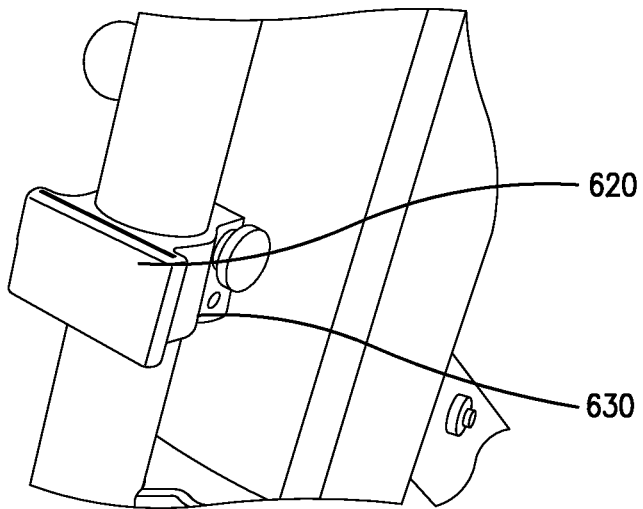
FIG. 22: Close up view of the outlet strip brackets in a stored configuration. The outlet strip brackets are translationally connected to the mobility assistance device so that they may be vertically positioned to any desired height and, when not in use, nested together.
Figure 23:
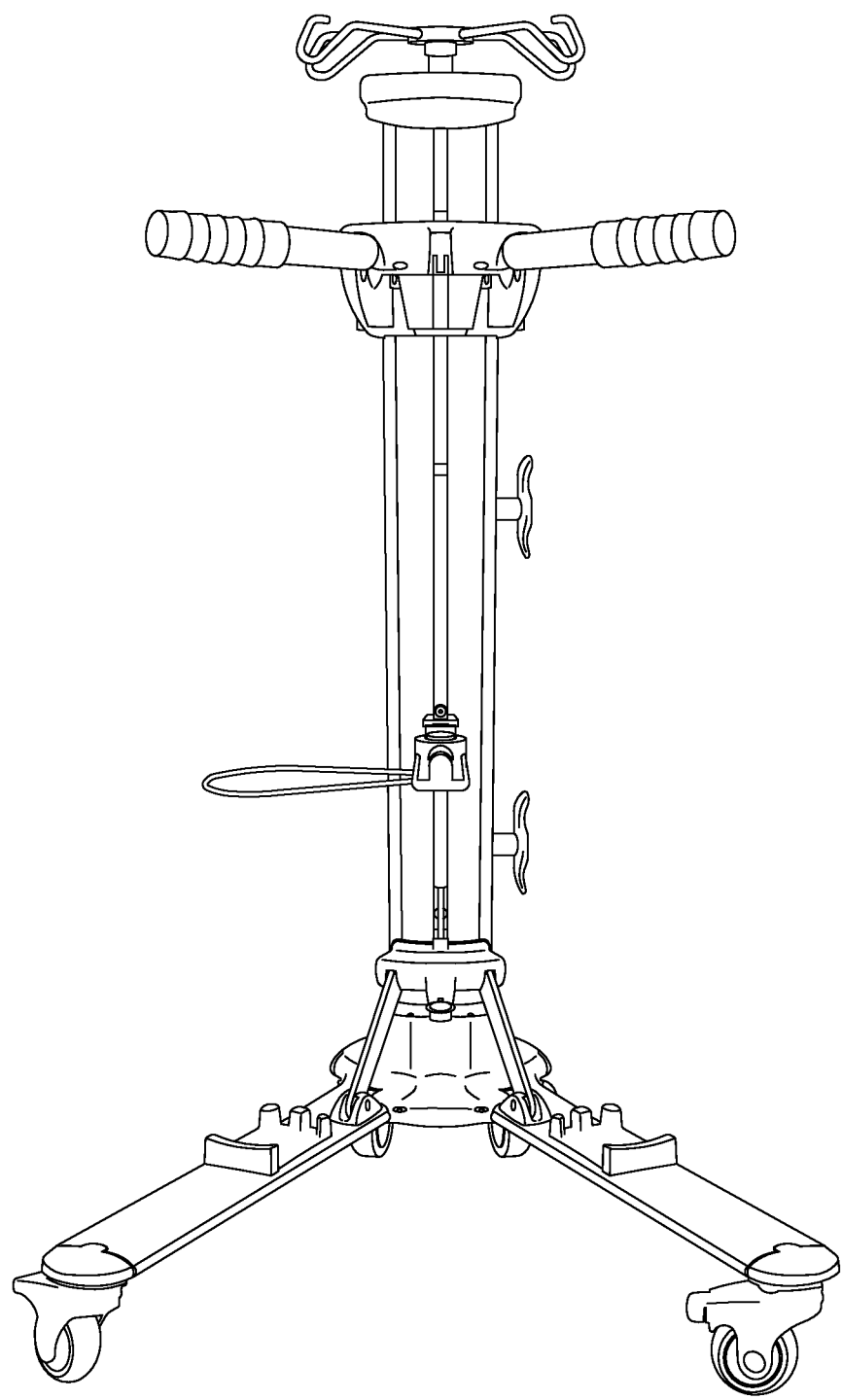
FIG. 23: Rear view of a mobility assistance device with various components deployed.
Figure 24:
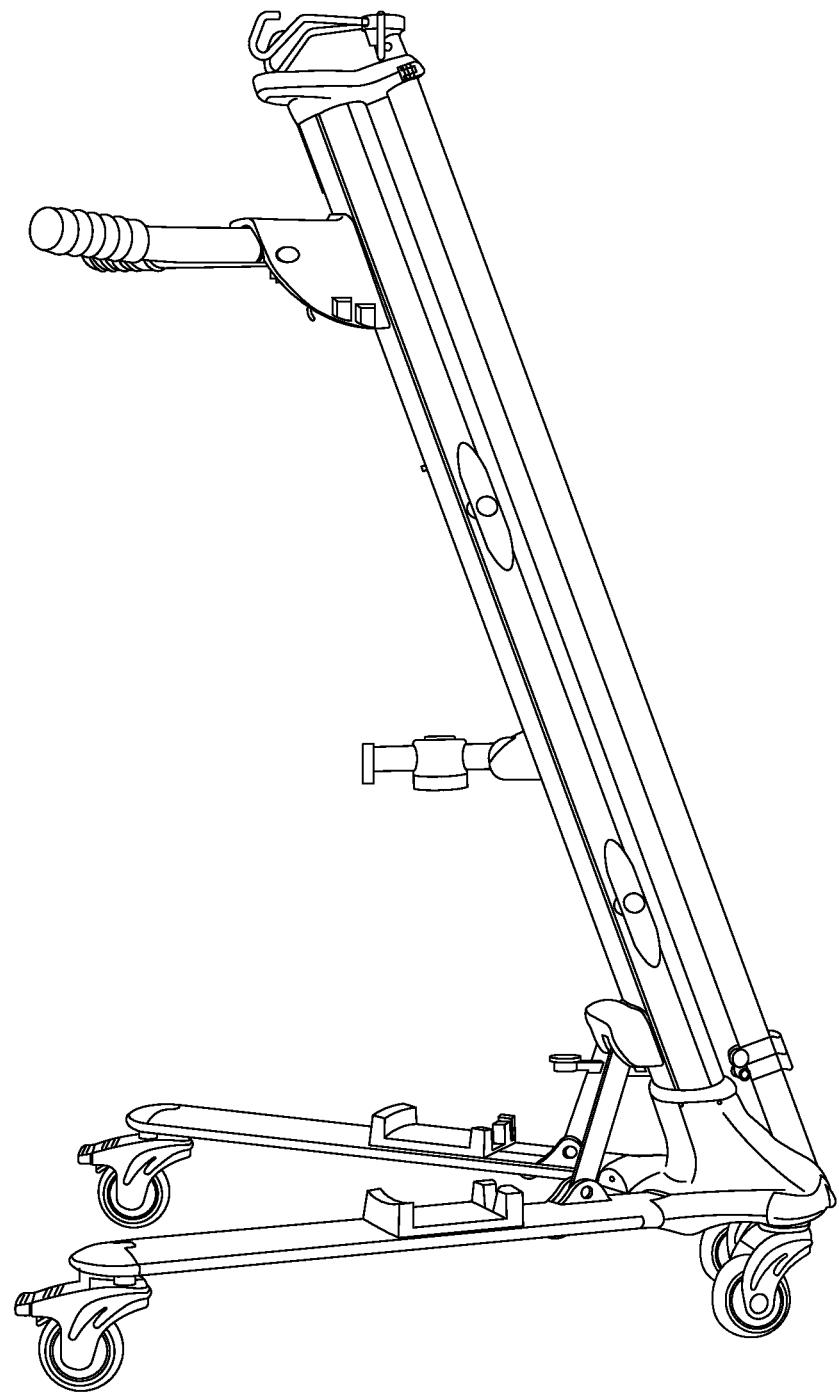
FIG. 24: Side view of the mobility assistance device of FIG. 23.

It may be desirable for any of the mobility assistance devices provided herein to be connected to electrical power. FIGS. 18-22 illustrate one example of a mobility assistance device configured for electrical power connection. In an aspect, the electrical power is provided by an electrical outlet strip 610, wherein the electrical outlet strip is in turn connected to a source of power, such as a wall outlet (e.g., stationary situations) or a battery (e.g., electrical power during ambulation is desired). Electrical outlet strip 610 may be mounted to the device in any convenient location, such as the base leg, mast or pole. FIGS. 20-22 illustrate an embodiment where the outlet strip is mounted to the pole 60 via outlet strip mount comprising a top bracket 620 and a bottom bracket 630 connected to the first 622 and second 632 ends of the outlet strip. Alternatively, outlet strip mount may be a single bracket that secures opposed sides of the outlet strip. FIG. 21 shows the brackets may be rotably connected to the pole so as to provide the ability of power strip to face different directions. Similarly, brackets may also translate up and down along the pole so as to accommodate strips of different lengths or to vertically position the strip at a desired height. FIG. 22 shows that when a power strip is not connected, the brackets 620 and 630 may be configured to nest with each other, thereby taking up minimal space on the pole. Such a nesting is also referred to as a bracket stored configuration. The brackets may have a locking mechanism to facilitate positioning of the brackets, such as by a thumb screw that is loosened for positioning and tightened once the desired position is obtained to lock the bracket in place.

Figure 18:
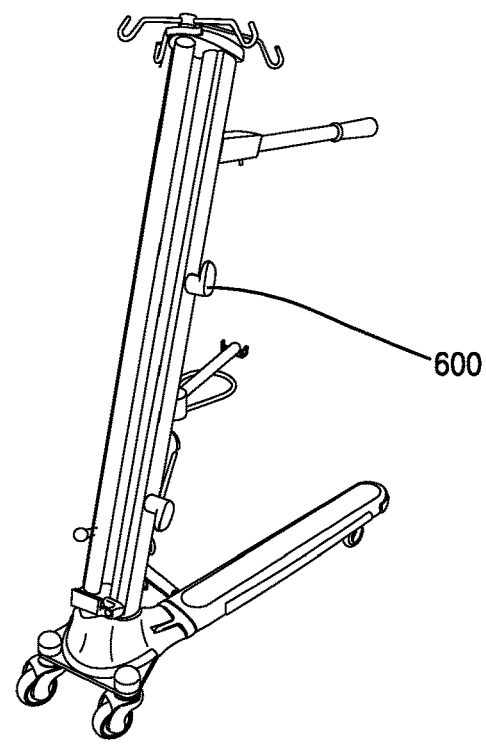
FIG. 18: Photograph of a mobility assistance device with power cord management brackets. The brackets may be deployable and storable via an articulation mechanism.
Figure 19:
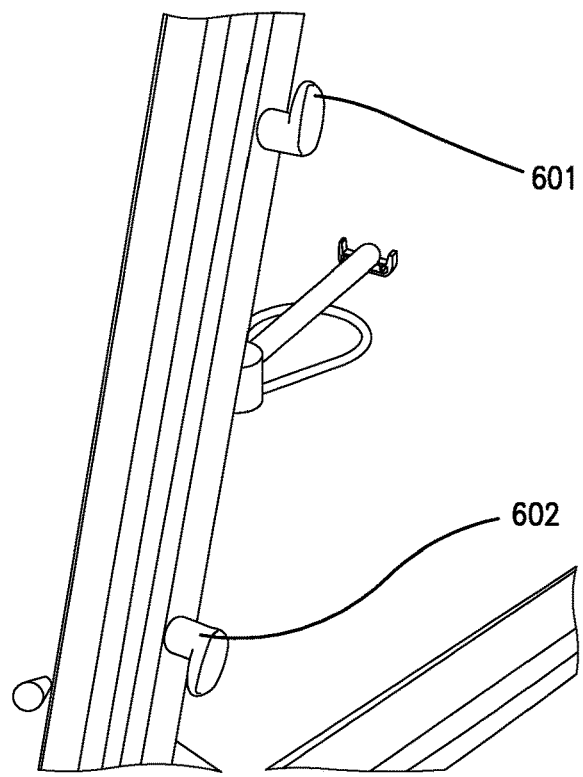
FIG. 19: Close-up view of the power cord management brackets.

FIGS. 18-19 show a power cord management system 600 comprising a first cord management bracket 601 and a second cord management bracket 602. Such brackets provide a convenient system for storing cords, including for example, a power outlet strip cord. The cord may be wrapped over the brackets 601 and 602, such as excess cord or when the outlet strip is not plugged into an electrical wall outlet but it is desired to keep the outlet strip with the mobility assistance device. The distance between brackets 601 and 602 over the mast surface is referred specifically as a "longitudinal portion of a mast surface."

Any of the cord brackets described herein may comprise an articulating cord hook. An articulating cord hook may be designed to have a larger footprint for receiving, for example, long lengths of relatively thick cords that are often associated with medical devices. When the cord is not needed, the articulation allows the hook to be positioned in a closed configuration so that the hook aligns with the mast surface. During use, the hook may be opened and extended from the mast. A leaf spring may be used to provide the ability to snap open and close the articulating cord hook.

FIGS. 23-35 show additional embodiments of a mobility assistance device and/or infusion management system. FIGS. 23-26 illustrate the various components of the device in a deployed or stored configuration, including for example, the mobility handle, oxygen tank holder, mounting arm (compare FIGS. 23-24 with FIG. 25) and base legs (compare FIGS. 23-25 with FIG. 26). Also shown is a geometrical configuration of the mobility handles characterized as a "swept-out" configuration. Swept-out refers to a portion of the mobility handle having an angle or curvature formed between the proximal 710 and distal 720 ends of the mobility handle (FIG. 28 right panels). In an aspect, the proximal and distal ends form an angle selected from a range that is greater than or equal to 90° and less than or equal to 160°. In an aspect, the swept-out configuration mobility handles remain within a confine of the deployed base footprint, or a substantial portion thereof, such as at least about 80%, 60% or 40% of the linear length positioned in a region that vertically coincides with the base footprint region. In an aspect, the proximal end 710 is aligned in a substantially parallel configuration with an underlying base leg, and the distal end sweeps in an outward direction relative to the center-line of the device. Such a configuration improves ergonomics, provides a wider hand spread, and better clearance when the handles are in a stored or stowed configuration (see, e.g., FIGS. 26-27).

An important feature includes the ability to "over-center" the base arms or base legs. For example, gas spring (see 170 of FIG. 9) forces the base legs tightly against the mast, eliminating the need for a catch or fastener to keep the legs in place in the stored configuration. Deployment requires lifting the top end of the mast and pushing each leg away from the mast past the over-center point. Once the leg is forced past the over-center point, they are readily moved to a deployed configuration. This arrangement is advantageous in that it keeps the legs much more tidy and eliminates the need for a separate leg deployment or release handle.

Figure 27:
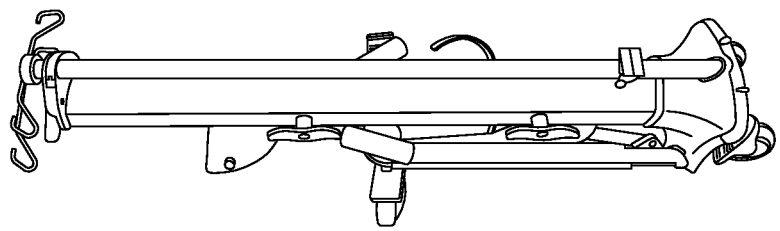
FIG. 27: Mobility assistance device in a fully stored configuration and resting against a floor ready for storage in a horizontal configuration, including underneath a bed.
Figure 28:
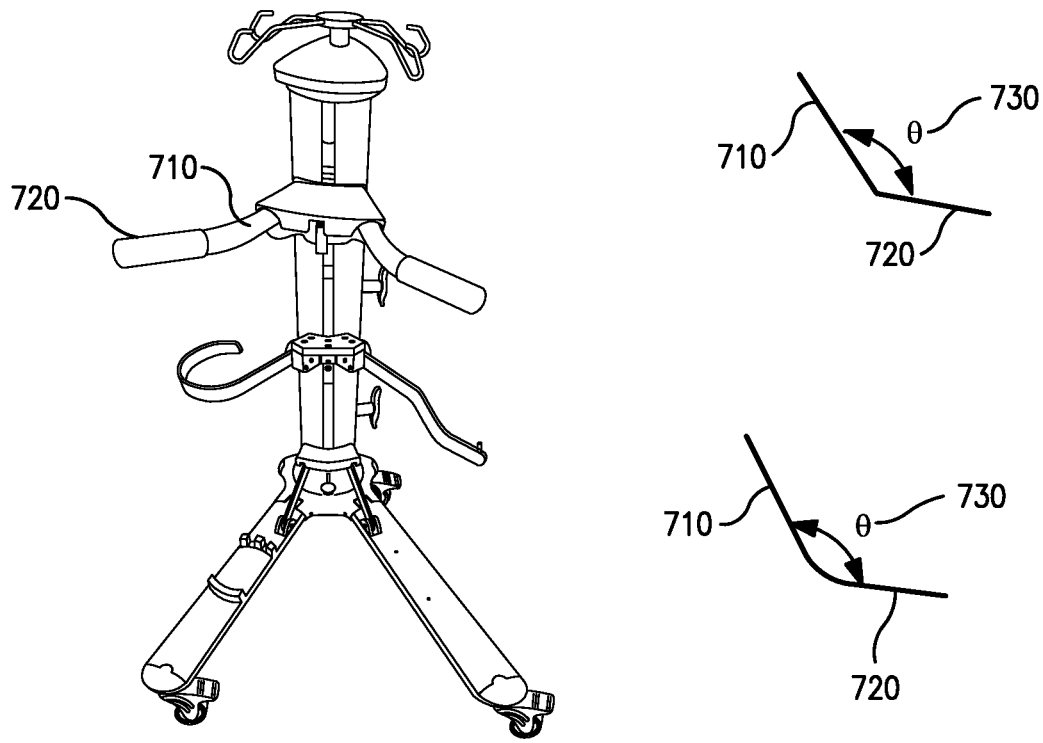
FIG. 28: Deployed mobility assistance device illustrating another shaped handle configuration, wherein the handles are in an angled outward geometry.

FIG. 28 illustrates mobility handles having a geometric configuration that angle outward (swept-out configuration), thereby improving ergonomics, providing better control with a wider hand-spread, and improving clearance when the handles are stored (see, e.g., FIG. 27). FIG. 28 also schematically illustrates the geometric configuration of the proximal and distal ends (710 720) as well as a sweep-out angle θ (730). In an aspect, the proximal and distal ends connect in a curved geometry (bottom right schematic), thereby avoiding sharp edges or corners. In an aspect, the proximal and distal ends connect to form a sharp angle (top right schematic). In an aspect, the sweep-out angle 730 is greater than about 90° and less than about 180°, such as between about 90° and 160°, any sub-ranges thereof, or about 145°.

Figure 30:
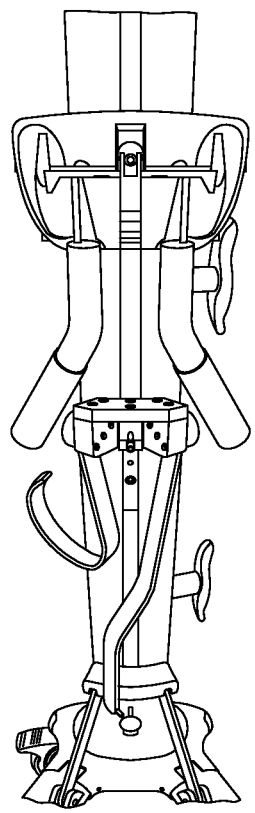
FIG. 30: Close up view of the shaped handle configuration with the oxygen canister holder and mounting arm in a stored configuration.
Figure 31A:
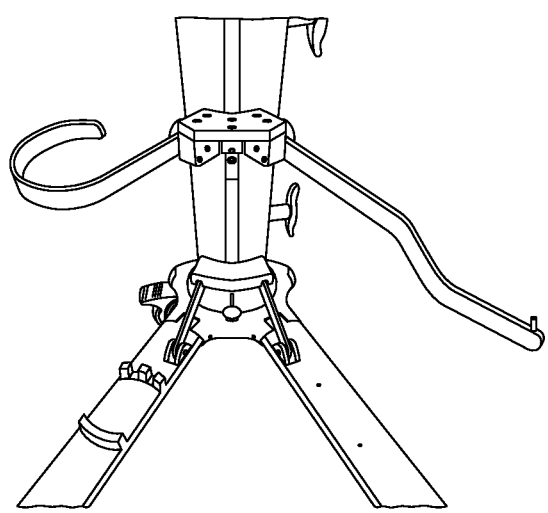
FIG. 31: Close up view of the oxygen canister holder and mounting arm: A deployed configuration and ready to receive devices; B holding an oxygen canister and medical device that is a pleur-evac; C in a stored configuration.
Figure 31B:
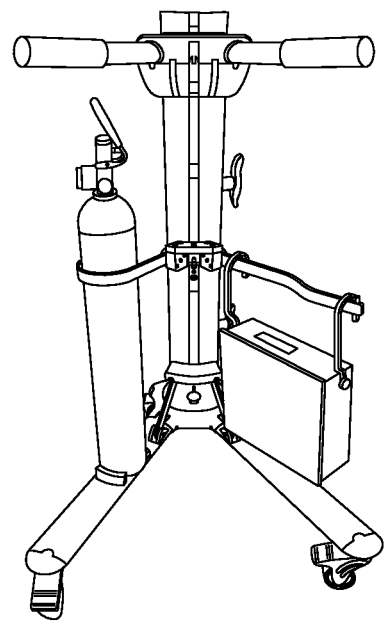
Figure 31C:
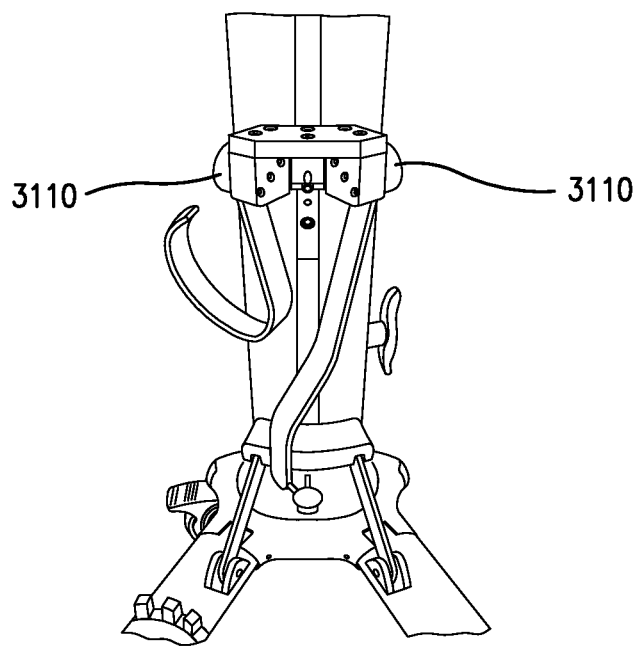
Figure 32A:
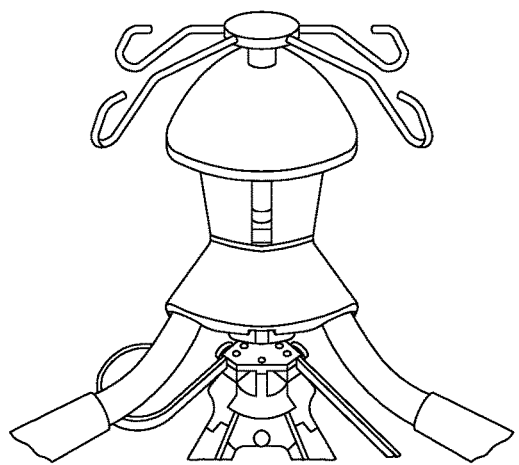
FIG. 32: A and B illustrate holders that swivel between a rearward and forward direction, respectively, in a pole-stored configuration. C and D illustrate holders that swivel between a rearward and forward direction, respectively, in a pole-deployed configuration.
Figure 32B:
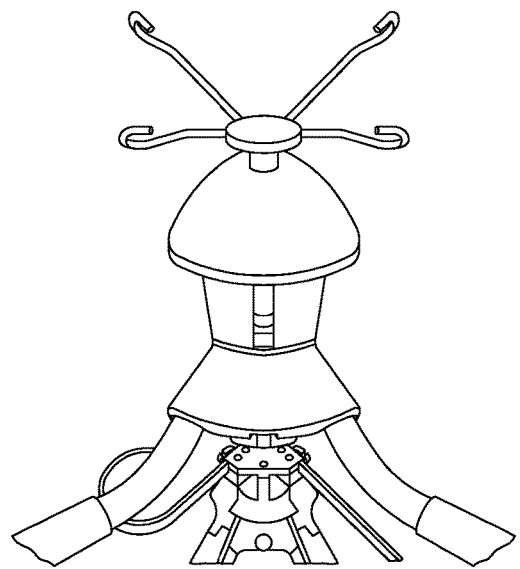
Figure 32C:
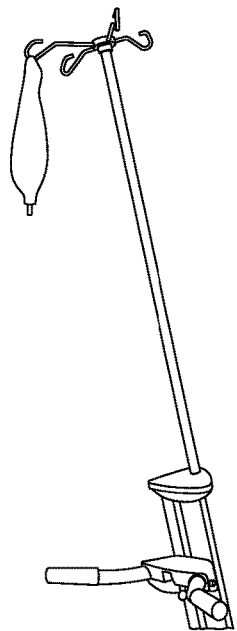
Figure 32D:
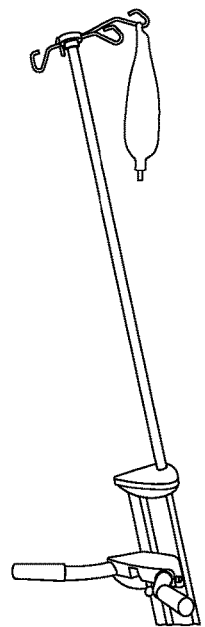

A close-up view of the mobility handle 70, oxygen tank holder 500, and mounting arm 150 in a deployed configuration is shown in FIG. 29. Those components are shown in FIG. 30 in a stored configuration. In an aspect, the mounting arm is to secure a pleur-evac. In an aspect, the mounting arm is curved. In an aspect, the mounting arm is straight. In an aspect, the mounting arm has a distal catch to prevent a medical device from sliding off the arm, including a pleur-evac. FIG. 31A is a close up view of the deployed oxygen tank holder and mounting arm, and FIG. 31B shows a corresponding oxygen tank and pleur-evac connected to the oxygen tank holder and mounting arm, respectively. Optionally, a hook (not shown) is centered in the bracket, protruding about 1 inch from the bracket, for holding a Foley bag. A deployment mechanism, illustrated in FIG. 31C as a pull knob 3110 may be extended to release mounting arm or tank holder for rotation into a stored configuration. For ease of deployment, the stored mounting arm or tank holder may be rotated into a deployed configuration without engaging pull knobs. Alternatively, a push button may be depressed to release mounting arm or tank holder for rotation into a stored configuration.

In an aspect, the IV bag hook apparatus 1400 comprising a plurality of holders 140 can swivel 180°. FIG. 32A-32D show the IV bag hook apparatus 1400 with holders 140 pointed toward a patient (FIGS. 32A and 32C "rearward deployed configuration") and away from a patient (FIGS. 32B and 32D "forward deployed configuration") in a pole stored (FIGS. 32A and 32B) and a pole deployed (FIGS. 32B and 32D) configuration. This aspect is particularly advantageous in that it permits movement of the bags and associated tubing forward and higher and is intended to provide taller patients better headroom and visibility when ambulating with the pole deployed to provide fluid bags in an up configuration. In addition, the hook apparatus 1400 can be quickly removed and reinstalled, as desired. Accordingly, in an embodiment the hook apparatus is removably connected to the pole.

Figure 33:
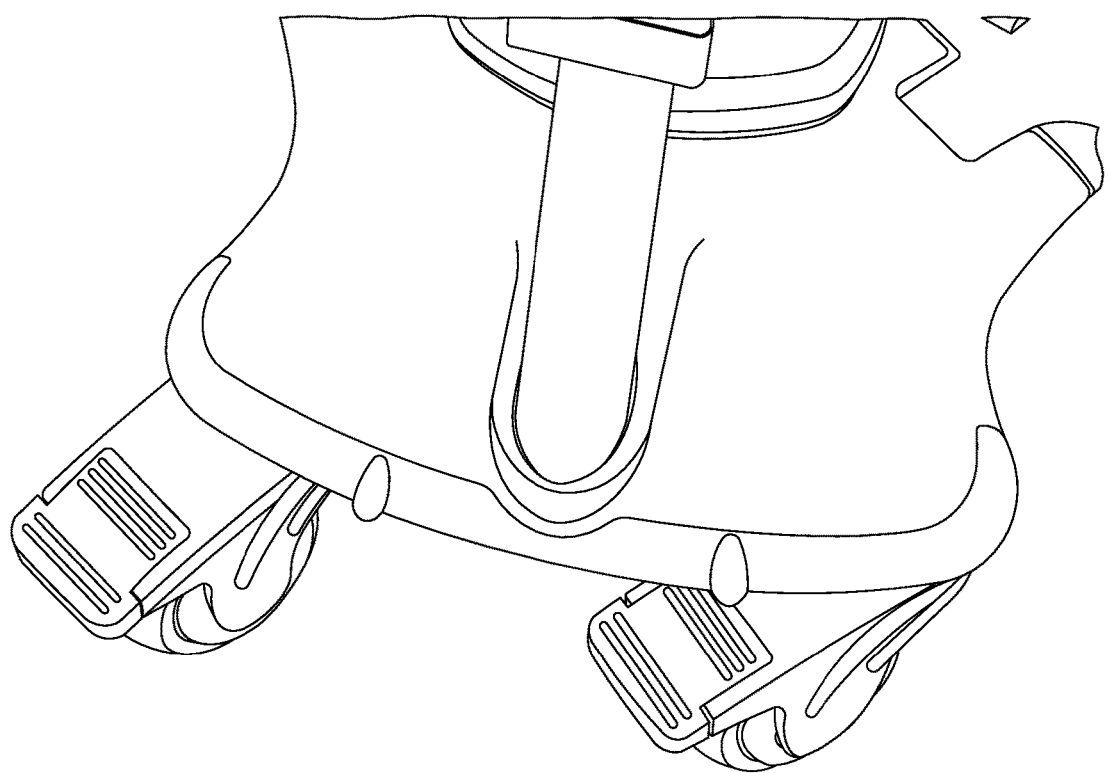
FIG. 33 illustrates an embodiment where brakes are operably connected to the front wheels. Also illustrated is the pole connected to the bottom of the mast region.

FIG. 33 illustrates the front wheels may be operably connected to brakes. For example, the casters may have brakes at the nose to provide easier access for a medical caregiver when positioning the device, such as at a bedside or toilet. In an aspect, all four wheels that support the device and connect to a ground surface are operably connected to brakes.

Figure 34:
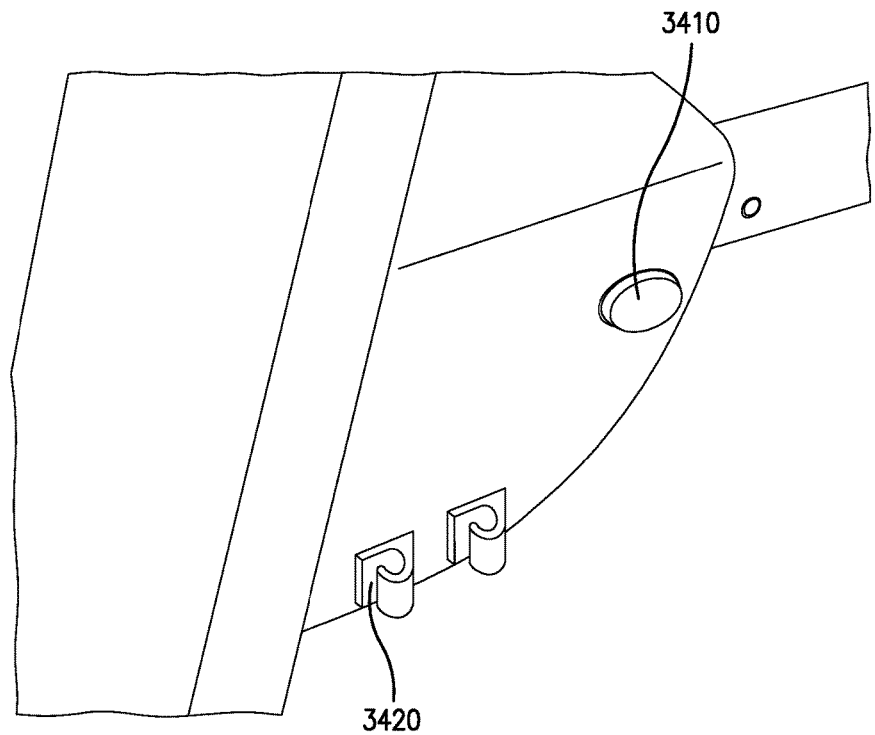
FIG. 34 is a close-up view of the mobility handle platform that connects the mobility handles to the mast with a deployment button and a pair of fasteners to secure tubing or cords, including IV tubing, to the device.

FIG. 34 is a close-up view of the mobility handle platform that connects the mobility handle to the mast with the engagement mechanism 78 (see, e.g., FIG. 8) provided in the form of an engagement button 3410 to release the handle when folding or rotating it into a stored position. A series of fasteners 3420 may be used to secure tubing or cords, including IV and oxygen tubing, to the device. In an embodiment, the number of fasteners on each side is greater than or equal to 2 and less than or equal to 6. In an aspect, there are four fasteners per side.

Figure 35:
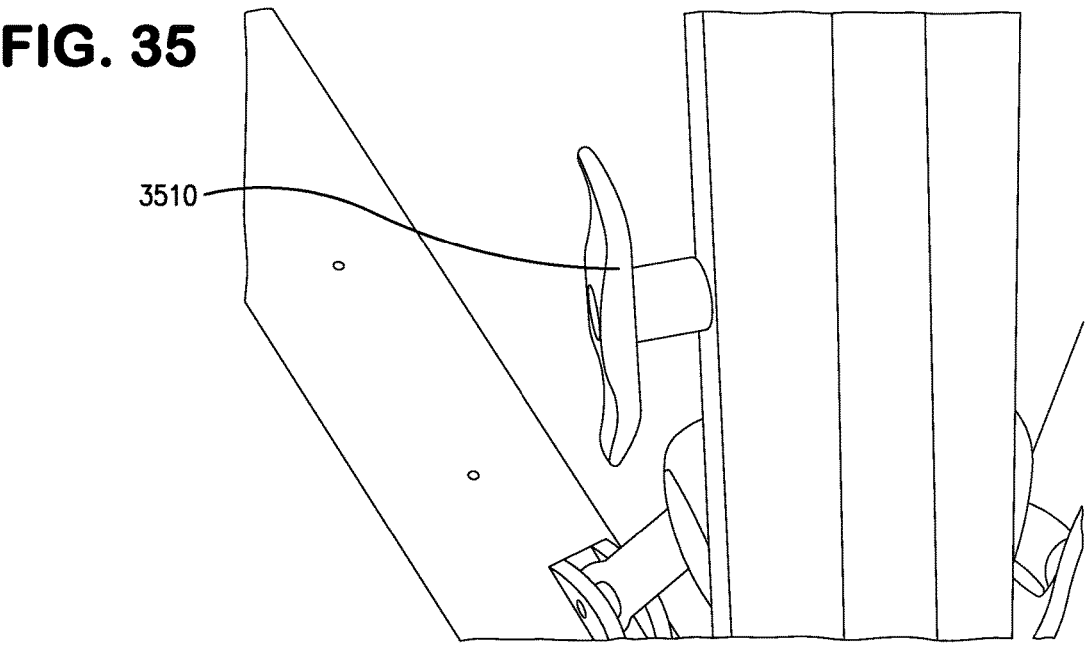
FIG. 35 illustrates a "T" shaped power cord management hook.

FIG. 35 illustrates a T-shaped power management hook 3510 connected to the mast or pole, for example. Other equipment may be hung or secured to the hook, as desired.

Figure 36A:
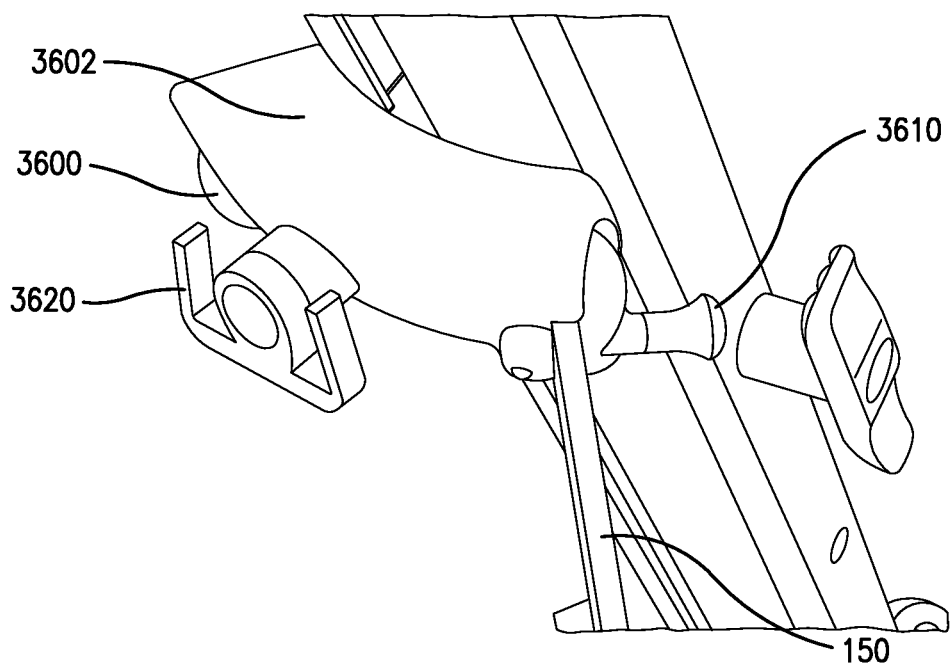
FIGS. 36A-36C illustrate an accessory module connected to the mast from which a mounting arm, pleur-evac mounting arm and oxygen tank upper holder (not shown) may extend.
Figure 36B:
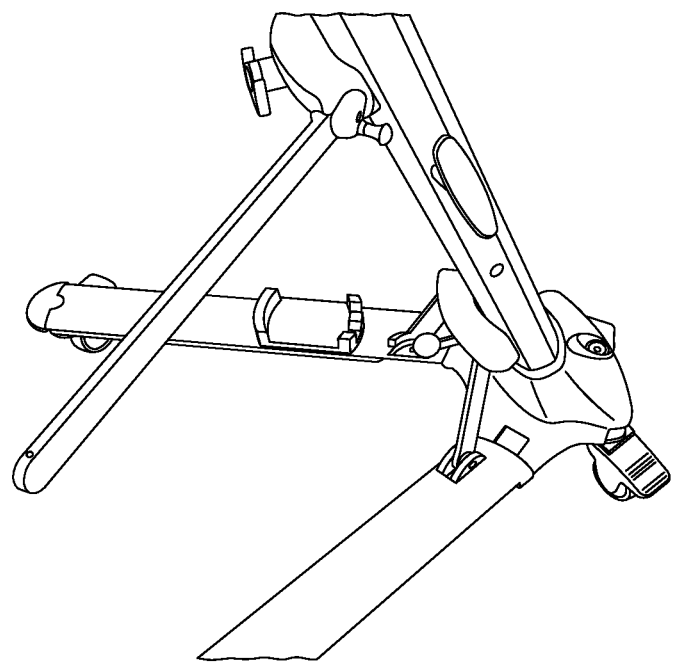
Figure 36C:
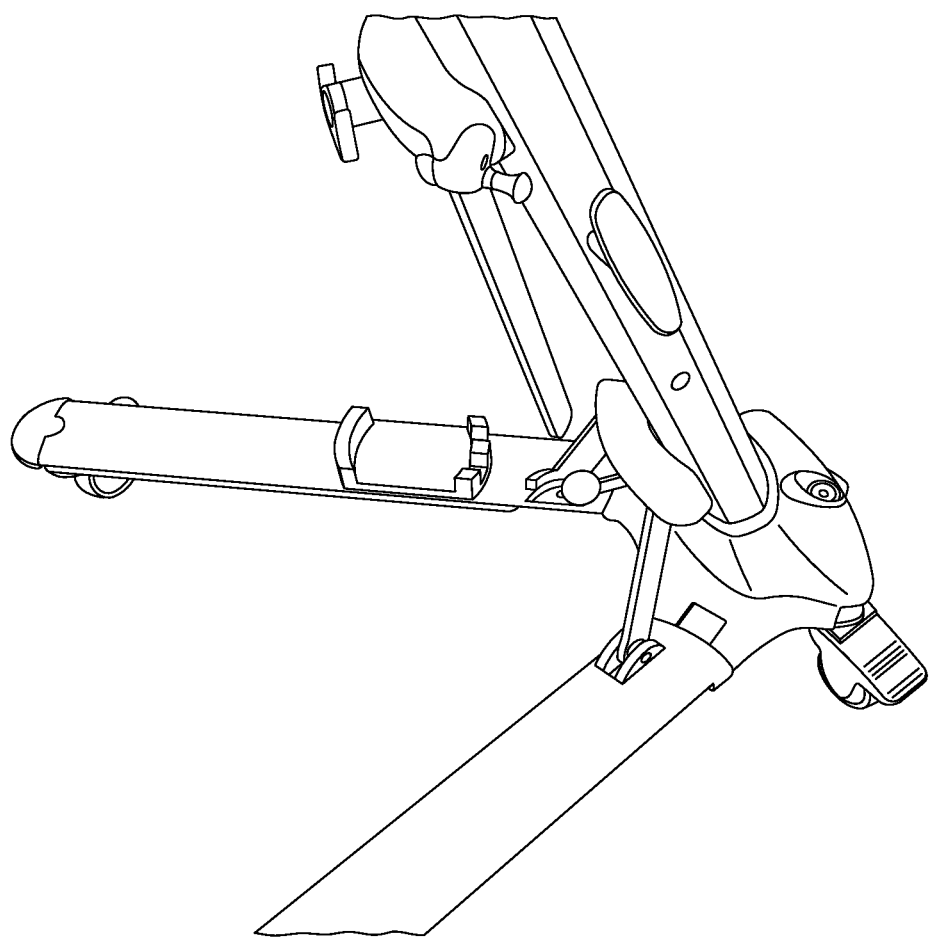

Any of the devices and methods provided herein may have an accessory module 3600 operably connected to the mast, as shown in FIGS. 36A-36C. An engagement mechanism 3610 may be used to facilitate deployment or storage of mounting arm 150, such as a mounting arm to hold a pleur-evac (FIG. 36A). The mounting arm may be rotably connected to the accessory module, including central portion 3602, such that engagement of the mechanism 3610 permits rotation of the mounting arm from a deployed configuration (FIG. 36B) to a stored configuration (FIG. 36C). Holders 3620 such as hooks, may connect to the accessory module and are useful for holding, for example, catheter bags. Alternatively, or in addition, holders may also connect to the mounting arm 150 (see, e.g., FIG. 10). An upper oxygen tank holder may extend from the accessory module at an opposite end from the mounting arm 150 (see, e.g., FIGS. 31-A-31C). As desired, any of the components extending from the accessory module may be independently removable, as desired. Alternatively, oxygen tank holder and mounting arm may be rotably connected to the accessory module so that when not required they are rotated to a stored configuration. The accessory module is optionally translationally connected to the mast to facilitate height adjustment of accessory module, via movement of central portion 3602 along the mast. The accessory module is optionally removably connected to the mast so that the entire accessory module may be removed, as desired. This may be useful for situations where the patient does not require the medical devices typically secured by the accessory module. The mounting arm and the upper oxygen tank holder may connect to the central portion at opposite ends, and the upper oxygen tank holder and the mounting arm may each extend in a direction that does not adversely interfere with accessibility of the base footprint. In this manner, a patient is able to stride within the base footprint without interference with the oxygen tank holder, mounting arm, or components connected thereto.

The features described herein provide a number of advantages. For example, the IV hooks may be readily removed and placed on the device, including individually or in combination. This is particularly useful for situations where a patient requires ambulation assistance but does not require IV fluid infusion, for example. The use of quick release clamps in any of the operable connections between components, such as the pump mount height adjustment and handle height adjustment ensures the components are safely maintained in a fixed position while preserving the ability to rapidly and safely adjust the height or deployment condition, for example. The bracket that holds the oxygen holder upper portion and the mounting arm allows for both the device to safely accommodate oxygen tanks and pleur-evac devices and to be used without them by storing the oxygen holder and mounting arm when not in use. A gas spring is particularly useful for a number of functions, including the ability to deploy the unit and keep the unit deployed by avoiding inadvertent collapse, and to tightly compact the device for storage and shipping.

EXAMPLE 7

Tether Connection

Figure 37:
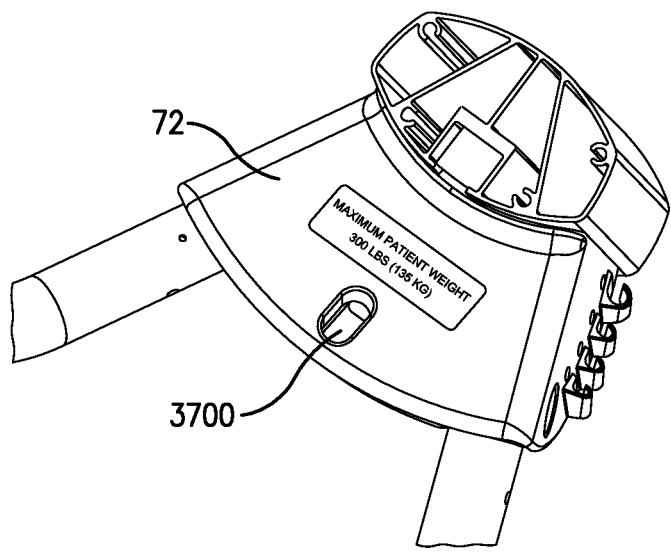
FIG. 37 illustrates a tether port through the platform or handle bracket that may be used to attach a tether to the device.
Figure 38:
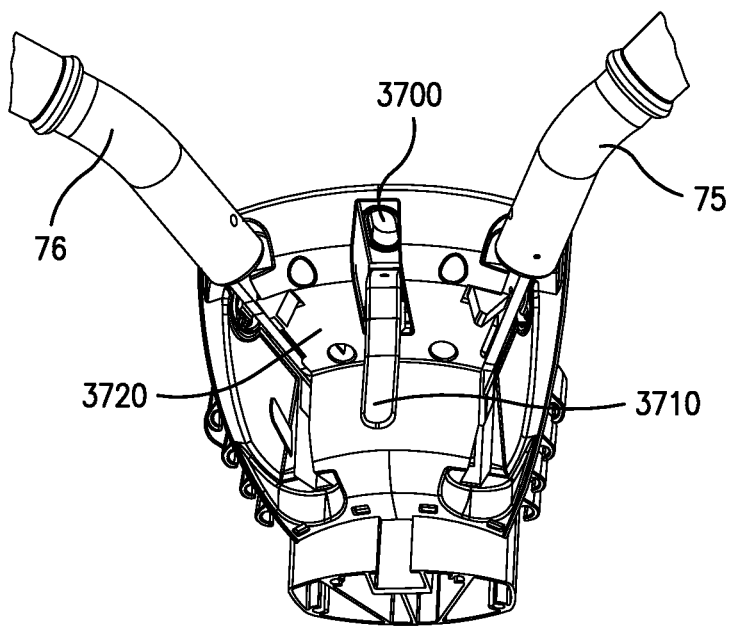
FIG. 38 is a bottom view of the tether port of FIG. 37.

In certain aspects, it may be desirable to secure the device to a patient and/or a medical caregiver. In this manner, the risk of a runaway device event is minimized. For example, a tether may attach a patient to the device via a carabiner. Alternatively, a gait belt may be used. The other end of the tether or belt may be secured to the device. As illustrated in FIGS. 37-38, a tether port 3700 is positioned through the mobility handle platform 72. The port may be centered along a centerline of the platform and can, for example, be oval-shaped. A carabiner or similar device may snap through the tether port, with an attached tether extending to the patient's gait belt or other harness. The tether port goes through a structurally sound aluminum die casting of the handle bracket.

Also illustrated is the quick release cam 3710 extending beneath bottom surface 3720 of mobility handle platform 72 used for height adjustment of the handles 75 and 76. The tether port is configured to receive and anchor a tether. As desired, other features may be incorporated to alternatively secure a tether or other strap, such as Velcro® belts, loop and anchor, button fasteners, or the like to further secure the user to the device. In this aspect, the device is then secured to ensure it cannot travel too far from a user without adversely interfering with the user's stride or movement.

EXAMPLE 8

Wheelchair Attachment

Figure 39A:
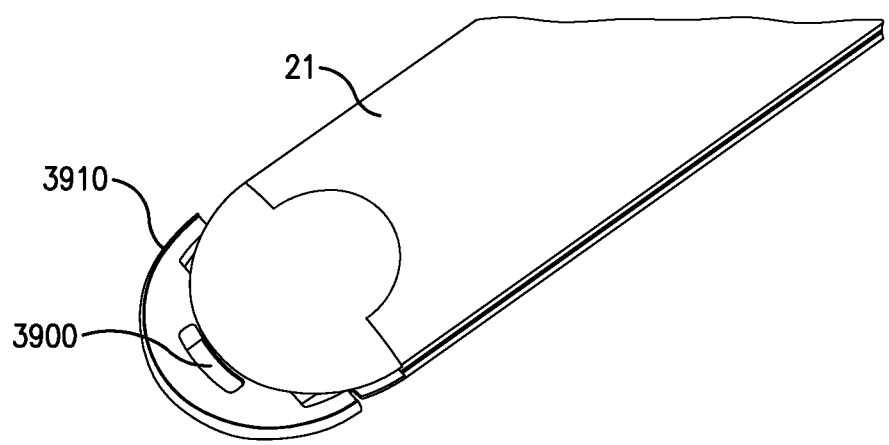
FIG. 39 illustrates an end portion of a base leg useful to secure a connector, such as for a wheelchair connector, via a connecting port at the end of a base leg. A The connecting port available and ready to receive one end of the connector. B. When the connecting port is not needed the hitch that provides the connecting port is retracted.
Figure 39B:
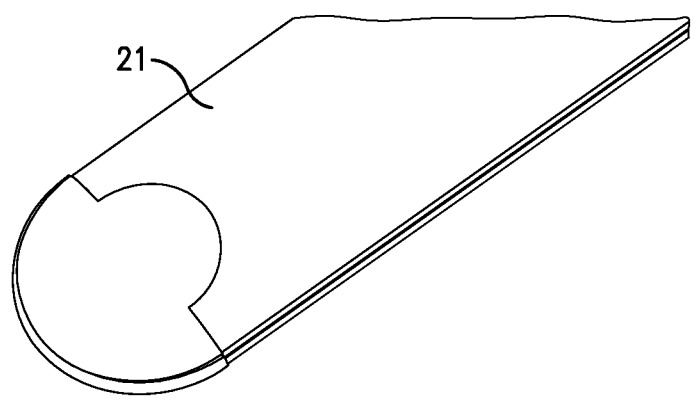
Figure 40:
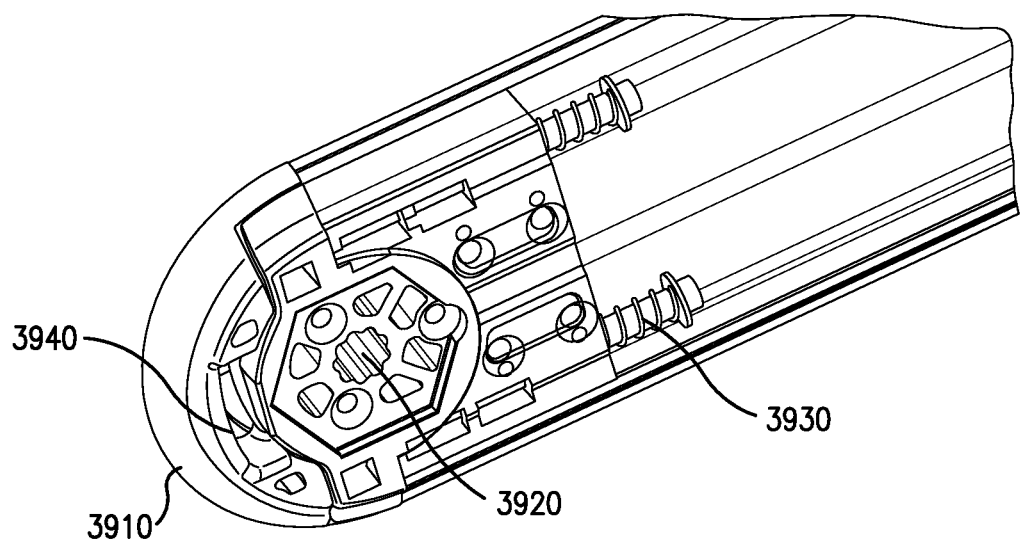
FIG. 40 is a bottom view of FIG. 39B illustrating mechanisms that may be used with the hitch to provide hitch deployment (FIG. 39A) and hitch retraction or storage (FIG. 39B).

The device may also be connected to another mobility device, such as a wheelchair. In this aspect, then, the user may be moved in the wheelchair and the mobility device of the instant invention connected thereto. An example of a mechanism to receive a connector that can, in turn, connect to a wheelchair, is provided in FIGS. 39-40. For example, a deployable connection port 3900 is operably connected to the first base leg 21 or, equivalently, the second base leg (FIG. 39A). FIG. 39B illustrates, when the connection port is not needed (e.g., the user is not in a wheelchair), the deployable connection port is stored beneath the base leg 21 in a stored configuration. The deployable connection port 3900 may be formed within deployable hitch 3910. FIG. 40 illustrates one mechanism that may be used to operably (e.g., movably) connect the deployable connection port to the base leg. Springs 3930 keep the hitch in a retracted or stored position, resulting in connection port 3900 that is effectively hidden beneath the base leg. A finger grip 3940 may be provided in bottom surface of hitch 3910 to facilitate deployment of the connection port 3900. In this aspect, the deployable connection port is configured to receive a connector that connects another ambulatory device, such as a wheelchair, to the device. When not required, however, the deployable connection port may be stored. In an aspect, a pair of connection ports is provided, one on each base leg. In this manner, two connectors are reliably connected to each side of the device and, accordingly, to the left and right sides of the wheelchair. This results in a substantially rigid and fixed connection between the wheelchair and the instant mobility device, allowing one caregiver (nurse) to push the wheelchair and mobility device together as one unit. With conventional equipment, a second caregiver is usually required move an IV pole while the primary caregiver pushes the wheelchair with patient.

All references cited throughout this application, for example patent documents including issued or granted patents or equivalents; patent application publications; and non-patent literature documents or other source material are hereby incorporated by reference in their entireties, as though individually incorporated by reference, to the extent each reference is not inconsistent with the disclosure in this application (for example, a reference that is partially inconsistent is incorporated by reference except for the partially inconsistent portion of the reference). In particular, U.S. Pat. Nos. 8,136,773 (173-06), 8,534,616 (173-06A), 8,662,458 (153-09), and U.S. Pat. Pub. No. 2013/0270799 filed Mar. 14, 2013 (173-06B) are specifically incorporated by reference for the devices, components, layout and connections described therein.

Every formulation or combination of components described or exemplified herein can be used to practice the invention, unless otherwise stated.

Whenever a range is given in the specification, for example, a size range or an angle range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference in their entirety to indicate the state of the art as of their publication or filing date and it is intended that this information can be employed herein, if needed, to exclude specific embodiments that are in the prior art.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein may be practiced in the absence of any element or elements, limitation or limitations which is not specifically disclosed herein.

One of ordinary skill in the art will appreciate that materials and methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

We claim:

1. A mobility assistance device comprising:
   a mast having a top end, a bottom end and an outer surface extending between the top and bottom ends;
   a base comprising a first base leg and a second base leg to form a two-sided base footprint, wherein one end of each of the first and second base legs connect to the mast to form a vertex region, and the mast and two-sided base footprint form a mast angle, wherein the mast angle is an acute angle so that at least a portion of the mast extends within a region that vertically extends from the two-sided base footprint;
   a pole connected to the mast for securing a medical component, wherein the pole has a longitudinal axis that is separated from the mast outer surface by a separation distance, wherein the pole is positioned externally to and at least partially alongside the mast and the separation distance is configured to provide a space between the mast and the pole for securing one or more medical components;
   a mobility handle connected to said mast or said base;
   a first wheel connected to said first base leg;
   a second wheel connected to said second base leg;
   a third wheel connected to said vertex region, wherein each of the wheels are configured to stably contact a support surface on which the device rests and the mobility handle is configured to receive an applied force to stably ambulate the device over the support surface;
   a gas spring operably connected to the base legs and the mast, wherein in a device stored configuration the gas spring forces the base legs to over-center and tightly nest to the mast.

2. The device of claim 1, wherein the pole is:
   extendible to provide a pole top end that is controllably extended relative to the mast top end, wherein the pole top end:
      has a selectable separation distance from the mast top end that is greater than 0 cm and less than or equal to 1 m; or
      is substantially parallel to a longitudinal axis of the mast or the mast outer surface; or
      has both: a selectable separation distance from the mast top end that is greater than 0 cm and less than or equal to 1 m; and is substantially parallel to a longitudinal axis of the mast or the mast outer surface.

3. The device of claim 1, wherein the pole is connected to a top portion of the mast and a bottom portion of the mast, wherein:
   the pole comprises an upper pole portion and a lower pole portion, wherein the upper and lower pole portions are telescopingly connected to provide an extendible pole having a pole length that is adjustable;
   the connection between the pole and top portion of the mast comprises a top connector that extends from the mast top end and has a passage for receiving the pole; and
   the connection between the pole and bottom portion of the mast comprises a bottom connector for securing a bottom portion of the extendible pole to the mast bottom end.

4. The device of claim 1, wherein the pole has a pole top end, the device further comprising a holder connected to the pole top end for securing a medical component.

5. The device of claim 4, wherein the holder comprises a plurality of holders that each extend from the pole top end in a non-forward facing direction, wherein a first and second holder are extendably opposed to each other in a left and a right direction relative to the device, and at least two additional holders are evenly rotationally spaced and extend in a rearward-facing or a forward-facing direction, and the holders are rotationally connected to the pole top end, the rotational connection providing a holder forward deployed configuration and a rearward stored configuration.

6. The device of claim 1, wherein the mast angle is selected from a range that is greater than or equal to 50° and less than or equal to 85°.

7. The device of claim 1, further comprising a mounting arm connected to the mast and extending in a direction that is within the region that vertically extends from the two-sided base footprint, wherein the mounting arm is rotatably connected to the mast to provide a mounting arm deployed configuration and a mounting arm stored configuration.

8. The device of claim 1, wherein the mobility handle is translationally connected to the mast, and the mobility handle longitudinally translates over at least a longitudinal portion of the mast between the top end and the bottom end to provide height adjustability of the mobility handle and a controllable height adjustability selected from a vertical height relative to the base that is greater than or equal to 2 feet and less than or equal to 6 feet.

9. The device of claim 1, wherein the mobility handle further comprises:
   a platform having a first platform end and a second platform end opposibly facing each other;
   a first grip handle connected to the second platform end;
   a second grip handle connected to the second platform end;
   wherein the first platform end is translationally connected to the mast to provide longitudinal translation along the mast; the first and second grip handles are connected to the platform and extend from the platform along a plane that is substantially parallel to a base plane defined by the first and second base legs.

10. The device of claim 9, wherein the first grip handle and the second grip handle are removably or rotatably connected to the platform to provide a grip handle deployed configuration and a grip handle stored configuration.

11. The device of claim 1, wherein the mobility handle comprises a first grip handle and a second grip handle that are each linear and extend from the mast at a grip angle that is an acute angle, selected from a range that is greater than or equal to 30° and less than 90°.

12. The device of claim 1, wherein the mobility handle comprises a first grip handle and a second grip handle that each have at least a non-linear portion, wherein each of the grip handles comprise a proximal end and a distal end, the proximal end connecting the distal end to the mast, wherein the proximal end and the distal end connect in a swept-out configuration and at an angle selected from a range that is greater than or equal to 90° and less than or equal to 160°.

13. The device of claim 1, wherein each of the first and second base leg are rotably connected to the mast bottom end to provide a stored configuration wherein the base legs are substantially parallel to the mast and a deployed configuration wherein the base legs and mast form the mast angle acute angle.

14. The device of claim 1, further comprising an oxygen tank holder connected to the mast for securably holding an oxygen tank.

15. The device of claim 14, wherein the oxygen tank holder comprises:
an upper tank holder connected to the mast for coupling with an upper portion of an oxygen tank, wherein the upper tank holder comprises an arm having an internal passage through which an oxygen tank extends, and the arm is rotationally positionable relative to the first or second base leg; and
a lower tank holder connected to the first or the second base leg for coupling with a base portion of an oxygen tank, wherein the lower tank holder comprises a receiving surface and a circumferential lip for receiving a bottom surface of an oxygen tank.

16. The device of claim 1, wherein an application force is required to force the base legs from the over-center stored configuration.

17. The device of claim 1, further comprising:
a deployable connection port operably connected to the first base leg or the second base leg;
wherein the deployable connection port is configured to receive a connector that connects a wheelchair to the device.

18. A mobility assistance device comprising:
a mast having a top end, a bottom end and an outer surface extending between the top and bottom ends;
a base comprising a first base leg and a second base leg to form a two-sided base footprint, wherein one end of each of the first and second base legs connect to the mast to form a vertex region, and the mast and two-sided base footprint form a mast angle, wherein the mast angle is an acute angle so that at least a portion of the mast extends within a region that vertically extends from the two-sided base footprint;
a pole connected to the mast for securing a medical component, wherein the pole has a longitudinal axis that is separated from the mast outer surface by a separation distance, wherein the pole is positioned externally to and at least partially alongside the mast and the separation distance is configured to provide a space between the mast and the pole for securing one or more medical components;
a mobility handle connected to said mast or said base;
a first wheel connected to said first base leg;
a second wheel connected to said second base leg;
a third wheel connected to said vertex region, wherein each of the wheels are configured to stably contact a support surface on which the device rests and the mobility handle is configured to receive an applied force to stably ambulate the device over the support surface;
a fourth wheel connected to the vertex region, wherein the third and fourth wheels are aligned with respect to each other and separated by a separation distance that is greater than or equal to 5 cm and less than or equal to 50 cm;
a fifth wheel and a sixth wheel that are trolley wheels connected to the vertex region or the base, wherein the fifth wheel and the sixth wheel are each in a rearward-offset position relative to the third wheel and vertically offset from each of the first, second, third and fourth wheels so that during ambulation of the device in a device deployed configuration the first through fourth wheels are configured to stably contact the support surface and the fifth wheel and the sixth wheel are configured to not contact the support surface.

19. A mobility assistance device comprising:
a mast having a bottom end and a top end;
a base comprising a first base leg and a second base leg to form a two-sided base footprint, wherein one end of each of the first and second base legs connect to the mast bottom end to form a vertex region, and the mast and base footprint form a mast angle having an acute angle so that the mast extends within a region that vertically extends from the two-sided base footprint;
a first wheel connected to said first base leg;
a second wheel connected to said second base leg;
a third wheel connected to said vertex region, wherein each of the wheels are configured to stably contact a support surface on which the device rests;
a height adjustable mobility handle connected to the mast, wherein the height adjustable mobility handle translates along at least a longitudinal portion of the mast between the top end and the bottom end, wherein the mobility handle is configured to receive an applied force to stably ambulate the device over the support surface under the applied force and has a platform with a lip around an outer circumferential portion to support a material within an inner portion of the platform and prevent sliding of the material off the platform; and
a pole connected to the mast for securing a medical component, wherein the pole has a longitudinal axis that is separated from the mast outer surface by a separation distance, wherein the pole is positioned externally to and at least partially alongside the mast and the separation distance between the pole and the mast provides a space to secure one or more medical components.

20. The mobility assistance device of claim 19, wherein the pole is connected to a top portion of the mast and a bottom portion of the mast, wherein a central portion of the pole is separated from the mast by the separation distance.

21. The mobility assistance device of claim 19, further comprising a fourth wheel connected to the vertex region, wherein the third and fourth wheels are substantially aligned and separated by a separation distance to form a leading edge, and the two-sided base footprint further comprises the leading edge having a length corresponding to the separation distance between the third wheel and the fourth wheel, thereby resulting in an open trapezoidal base footprint.

22. The mobility assistance device of claim 19, further comprising an oxygen tank holder for securably holding an oxygen tank to the mobility assistance device.

* * * * *